United States Patent
Rogers et al.

(10) Patent No.: US 12,220,305 B2
(45) Date of Patent: *Feb. 11, 2025

(54) SYSTEMS AND METHODS FOR TRANSCATHETER AORTIC VALVE TREATMENT

(71) Applicant: Silk Road Medical, Inc., Sunnyvale, CA (US)

(72) Inventors: Erica J. Rogers, Sunnyvale, CA (US); Michael P. Wallace, Sunnyvale, CA (US); Sumaira Macdonald, Sunnyvale, CA (US); Michi E. Garrison, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 1030 days.

This patent is subject to a terminal disclaimer.

(21) Appl. No.: 17/179,746

(22) Filed: Feb. 19, 2021

(65) Prior Publication Data

US 2021/0244522 A1 Aug. 12, 2021

Related U.S. Application Data

(63) Continuation of application No. 15/141,060, filed on Apr. 28, 2016, now Pat. No. 10,925,709.
(Continued)

(51) Int. Cl.
| A61F 2/01 | (2006.01) |
| A61F 2/24 | (2006.01) |
| A61M 25/06 | (2006.01) |

(52) U.S. Cl.
CPC ............ *A61F 2/013* (2013.01); *A61F 2/2436* (2013.01); *A61F 2002/016* (2013.01);
(Continued)

(58) Field of Classification Search
CPC .......... A61F 2/24; A61F 2/013; A61F 2/2436; A61F 2002/016; A61F 2/01; A61F 2/011;
(Continued)

(56) References Cited

U.S. PATENT DOCUMENTS

| 4,540,402 A | 9/1985 | Aigner |
| 4,808,156 A | 2/1989 | Dean |

(Continued)

FOREIGN PATENT DOCUMENTS

| CN | 103826571 A | 5/2014 |
| CN | 104582643 A | 4/2015 |

(Continued)

OTHER PUBLICATIONS

Henry et al. (1999) "Carotid stenting with cerebral protection: First clinical experience using the PercuSurge GuardWire System" J. Endovasc. Surg. 6:321-331.
(Continued)

*Primary Examiner* — Seema Mathew
(74) *Attorney, Agent, or Firm* — Seager, Tufte & Wickhem, LLP

(57) ABSTRACT

Devices and methods are configured to allow transcarotid or subclavian access via the common carotid artery to the native aortic valve, and implantation of a prosthetic aortic valve into the heart. The devices and methods also provide means for embolic protection during such an endovascular aortic valve implantation procedure.

11 Claims, 27 Drawing Sheets

Related U.S. Application Data

(60) Provisional application No. 62/210,919, filed on Aug. 27, 2015, provisional application No. 62/155,384, filed on Apr. 30, 2015.

(52) U.S. Cl.
CPC ............... *A61F 2230/0067* (2013.01); *A61F 2230/0069* (2013.01); *A61F 2230/0093* (2013.01); *A61M 2025/0681* (2013.01)

(58) Field of Classification Search
CPC .... A61F 2220/0008; A61F 2/82; A61F 2/014; A61F 2/2466; A61F 2/962; A61M 2025/0681
See application file for complete search history.

(56) References Cited

U.S. PATENT DOCUMENTS

| | | | |
|---|---|---|---|
| 6,413,235 B1 | 7/2002 | Parodi | |
| 6,423,032 B2 | 7/2002 | Parodi | |
| 6,454,799 B1 | 9/2002 | Schreck | |
| 6,514,226 B1 | 2/2003 | Levin et al. | |
| 6,595,953 B1 | 7/2003 | Coppi et al. | |
| 6,837,881 B1 | 1/2005 | Barbut | |
| 6,866,650 B2 | 3/2005 | Stevens et al. | |
| 7,083,594 B2 | 8/2006 | Coppi | |
| 7,491,163 B2 | 2/2009 | Viole et al. | |
| 8,298,169 B2 | 10/2012 | Yacoubian et al. | |
| 8,460,335 B2 | 6/2013 | Carpenter | |
| 8,545,432 B2 | 10/2013 | Renati et al. | |
| 8,858,490 B2 * | 10/2014 | Chou | A61M 27/00 604/9 |
| 9,126,018 B1 * | 9/2015 | Garrison | A61M 39/1011 |
| 9,241,699 B1 | 1/2016 | Kume et al. | |
| 10,039,906 B2 | 8/2018 | Kume et al. | |
| 10,085,864 B2 | 10/2018 | Chou et al. | |
| 10,159,479 B2 | 12/2018 | Hentges et al. | |
| 10,925,709 B2 * | 2/2021 | Rogers | A61F 2/013 |
| 11,433,226 B2 * | 9/2022 | Kume | A61M 1/3653 |
| 11,844,893 B2 * | 12/2023 | Drake | A61M 1/3673 |
| 12,070,542 B2 * | 8/2024 | McCarthy | A61M 39/10 |
| 2002/0049402 A1 | 4/2002 | Peacock et al. | |
| 2002/0128679 A1 | 9/2002 | Turovskiy et al. | |
| 2005/0154344 A1 | 7/2005 | Chang | |
| 2005/0154349 A1 | 7/2005 | Renz et al. | |
| 2005/0245892 A1 | 11/2005 | Elkins et al. | |
| 2006/0106338 A1 | 5/2006 | Chang | |
| 2009/0018455 A1 | 1/2009 | Chang | |
| 2009/0024072 A1 | 1/2009 | Criado et al. | |
| 2009/0198172 A1 | 8/2009 | Garrison et al. | |
| 2009/0240320 A1 | 9/2009 | Tuval et al. | |
| 2009/0254166 A1 | 10/2009 | Chou et al. | |
| 2010/0042118 A1 | 2/2010 | Garrison et al. | |
| 2010/0057096 A1 | 3/2010 | Wolf | |
| 2010/0185216 A1 | 7/2010 | Garrison et al. | |
| 2010/0191169 A1 | 7/2010 | Chang | |
| 2010/0191170 A1 | 7/2010 | Chang | |
| 2010/0204684 A1 | 8/2010 | Garrison et al. | |
| 2010/0217276 A1 | 8/2010 | Garrison et al. | |
| 2010/0228269 A1 | 9/2010 | Garrison et al. | |
| 2010/0280431 A1 | 11/2010 | Criado et al. | |
| 2011/0082408 A1 | 4/2011 | Chang | |
| 2011/0087147 A1 | 4/2011 | Garrison et al. | |
| 2011/0125131 A1 | 5/2011 | Chang | |
| 2011/0144690 A1 | 6/2011 | Bishop et al. | |
| 2011/0166496 A1 | 7/2011 | Criado et al. | |
| 2011/0166497 A1 | 7/2011 | Criado et al. | |
| 2011/0213459 A1 * | 9/2011 | Garrison | A61B 17/12122 623/2.11 |
| 2013/0172852 A1 | 7/2013 | Chang | |
| 2013/0197621 A1 | 8/2013 | Ryan et al. | |
| 2013/0281788 A1 * | 10/2013 | Garrison | A61B 17/221 606/127 |
| 2014/0031682 A1 | 1/2014 | Renati et al. | |
| 2014/0031925 A1 | 1/2014 | Garrison et al. | |
| 2014/0058414 A1 | 2/2014 | Garrison et al. | |
| 2014/0135661 A1 * | 5/2014 | Garrison | A61N 7/00 607/116 |
| 2014/0296769 A1 * | 10/2014 | Hyde | A61M 27/002 604/9 |
| 2014/0296868 A1 | 10/2014 | Garrison et al. | |
| 2014/0371653 A1 | 12/2014 | Criado et al. | |
| 2015/0025616 A1 | 1/2015 | Chang | |
| 2015/0080942 A1 | 3/2015 | Garrison et al. | |
| 2015/0141760 A1 | 5/2015 | Chou et al. | |
| 2015/0150562 A1 | 6/2015 | Chang | |
| 2015/0174368 A1 * | 6/2015 | Garrison | A61B 17/22 604/525 |
| 2015/0327843 A1 | 11/2015 | Garrison | |
| 2016/0128688 A1 | 5/2016 | Garrison et al. | |
| 2016/0158044 A1 | 6/2016 | Chou et al. | |
| 2016/0158502 A1 | 6/2016 | Kume et al. | |
| 2016/0166804 A1 | 6/2016 | Garrison et al. | |
| 2016/0242764 A1 | 8/2016 | Garrison et al. | |
| 2016/0271315 A1 | 9/2016 | Chang | |
| 2016/0271316 A1 | 9/2016 | Criado et al. | |
| 2016/0279379 A1 | 9/2016 | Chang | |
| 2016/0296690 A1 * | 10/2016 | Kume | A61M 39/06 |
| 2016/0317288 A1 * | 11/2016 | Rogers | A61F 2/013 |
| 2017/0043141 A1 | 2/2017 | Kume et al. | |
| 2017/0136212 A1 | 5/2017 | Garrison et al. | |
| 2017/0209260 A1 | 7/2017 | Garrison et al. | |
| 2017/0296798 A1 | 10/2017 | Kume et al. | |
| 2017/0312491 A1 | 11/2017 | Ryan et al. | |
| 2017/0354803 A1 | 12/2017 | Kume et al. | |
| 2017/0361072 A1 | 12/2017 | Chou et al. | |
| 2017/0368296 A1 | 12/2017 | Chang | |
| 2018/0008294 A1 | 1/2018 | Garrison et al. | |
| 2018/0154063 A1 | 6/2018 | Criado et al. | |
| 2018/0185614 A1 | 7/2018 | Garrison et al. | |
| 2018/0289884 A1 | 10/2018 | Criado et al. | |
| 2019/0105439 A1 | 4/2019 | Criado et al. | |
| 2019/0150916 A1 | 5/2019 | Hentges et al. | |
| 2019/0175885 A1 | 6/2019 | Kume et al. | |
| 2019/0231962 A1 | 8/2019 | Criado et al. | |
| 2019/0254680 A1 | 8/2019 | Chang | |
| 2019/0262530 A1 | 8/2019 | Criado et al. | |
| 2019/0269538 A1 | 9/2019 | Chou et al. | |
| 2019/0366070 A1 | 12/2019 | Kume et al. | |
| 2019/0388654 A1 | 12/2019 | Chou et al. | |
| 2020/0009406 A1 | 1/2020 | Garrison et al. | |
| 2020/0015826 A1 | 1/2020 | Chang | |
| 2020/0016321 A1 | 1/2020 | Criado et al. | |
| 2021/0244522 A1 * | 8/2021 | Rogers | A61F 2/013 |

FOREIGN PATENT DOCUMENTS

| | | |
|---|---|---|
| JP | 2011-507597 A | 3/2011 |
| JP | 2014-524813 A | 9/2014 |
| WO | WO-2009/085207 A1 | 7/2009 |
| WO | WO-2013/013021 A2 | 1/2013 |

OTHER PUBLICATIONS

U.S. Appl. No. 14/227,585, filed Mar. 27, 2014, US 2014-0296769.
U.S. Appl. No. 15/049,637, filed Feb. 22, 2016, US 2016-0242764.
U.S. Appl. No. 15/399,638, filed Jan. 5, 2017, US 2017-0209260.
U.S. Appl. No. 15/641,966, filed Jul. 5, 2017, US 2017-0296798.
U.S. Appl. No. 16/171,784, filed Oct. 26, 2018, US 2019-0125512.
U.S. Appl. No. 16/281,311, filed Feb. 21, 2019, US 2019-0388654.
U.S. Appl. No. 16/297,348, filed Mar. 8, 2019, US 2020-0038576.
U.S. Appl. No. 16/299,524, filed Mar. 12, 2019, US 2019-0366070.
U.S. Appl. No. 16/353,492, filed Mar. 14, 2019, US 2020-0009406.
U.S. Appl. No. 16/377,663, filed Apr. 8, 2019, US 2019-0231962.
U.S. Appl. No. 16/513,030, filed Jul. 16, 2019, US 2020-0170637.
U.S. Appl. No. 16/530,783, filed Aug. 2, 2019, US 2020-0054871.
U.S. Appl. No. 16/544,083, filed Aug. 19, 2019, US 2020-0171277.
U.S. Appl. No. 16/880,594, filed May 21, 2020, US 2020-0282127.
U.S. Appl. No. 16/894,474, filed Jun. 5, 2020, US 2020-0297912.
U.S. Appl. No. 16/906,457, filed Jun. 19, 2020, US 2020-0397472.

(56) References Cited

OTHER PUBLICATIONS

U.S. Appl. No. 16/939,396, filed Jul. 27, 2020, US 2020-0397446.
U.S. Appl. No. 16/999,634, filed Aug. 21, 2020, US 2020-0375728.
U.S. Appl. No. 16/999,640, filed Aug. 21, 2020, US 2020-0375729.
U.S. Appl. No. 17/000,004, filed Aug. 21, 2020, US 2020-0390437.
PCT/US2020/058365, Oct. 30, 2020, WO 2021/087363.
PCT/US2020/058588, Nov. 2, 2020, WO 2021/087470.

* cited by examiner

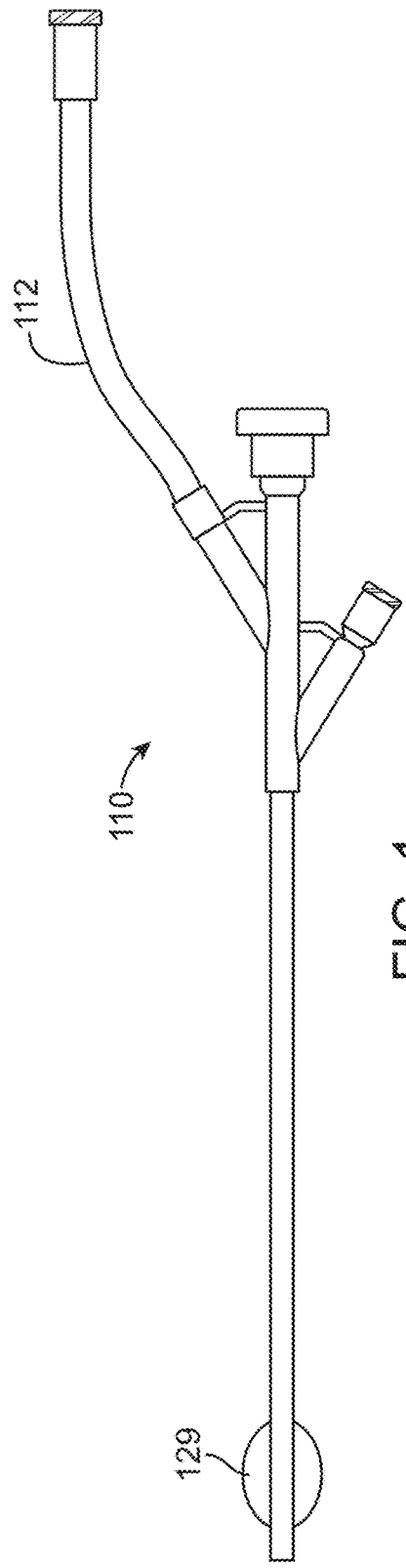
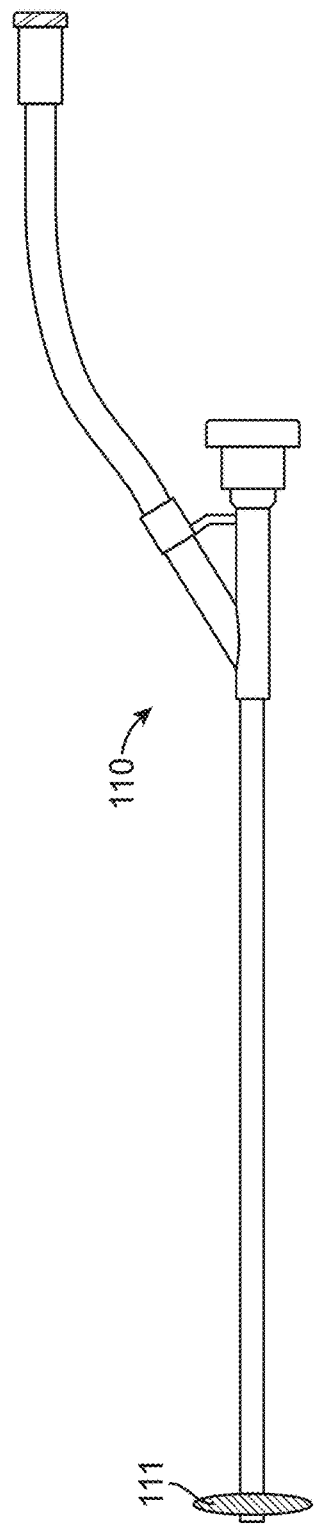
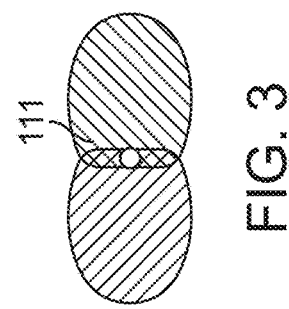
FIG. 1
FIG. 2
FIG. 3

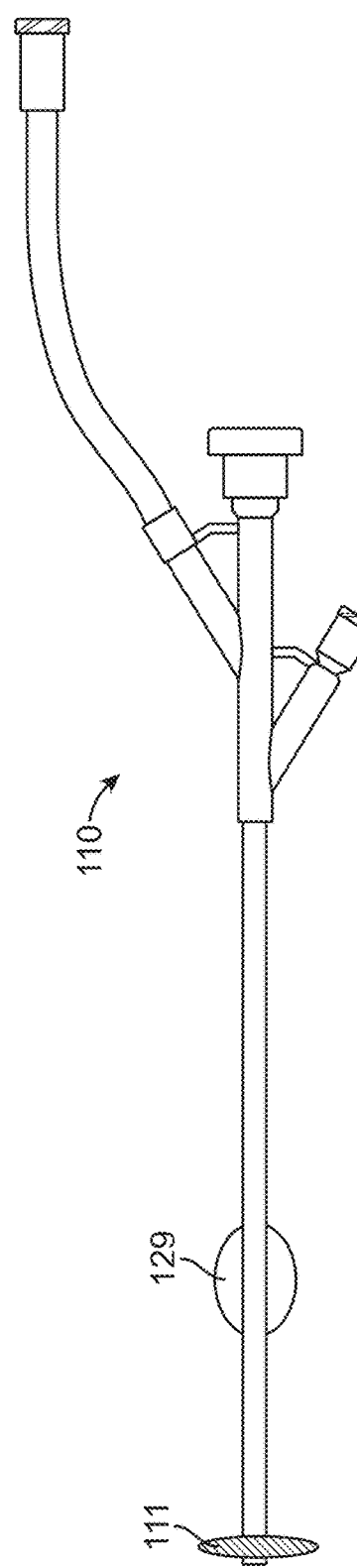
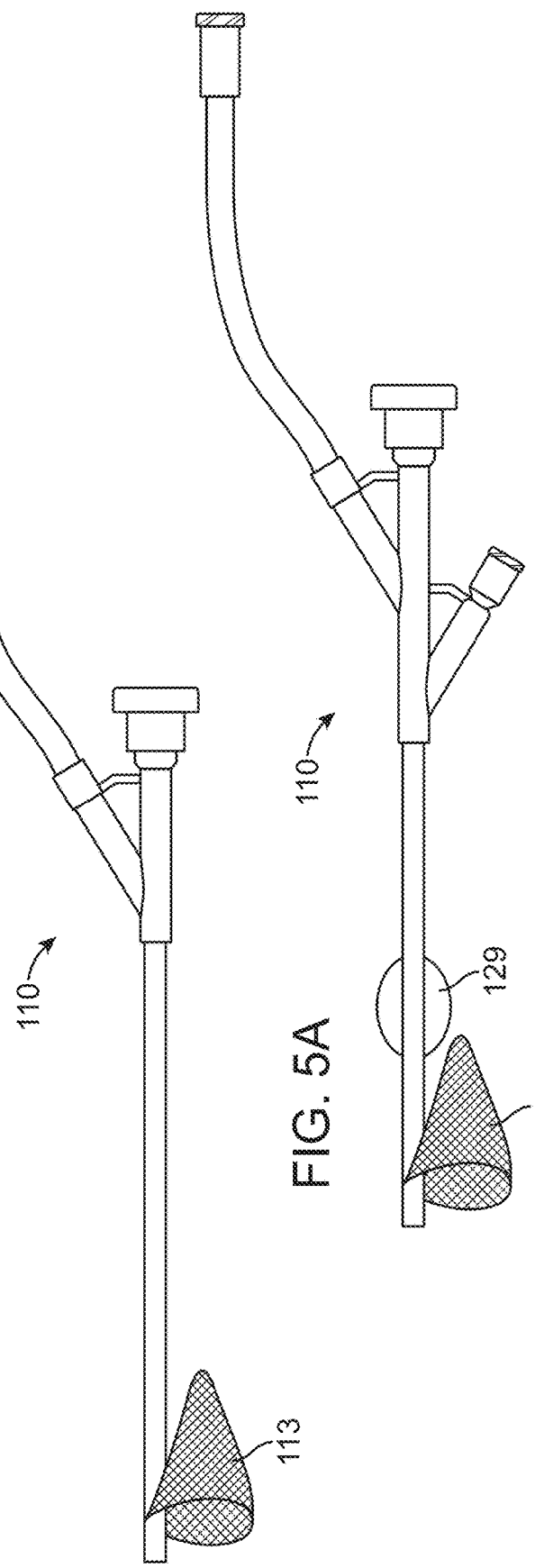
FIG. 4
FIG. 5A
FIG. 5B

SYSTEMS AND METHODS FOR TRANSCATHETER AORTIC VALVE TREATMENT

CROSS REFERENCE TO RELATED APPLICATIONS

This application is a continuation of U.S. patent application Ser. No. 15/141,060 filed Apr. 28, 2016, issuing on Feb. 23, 2021, as U.S. Pat. No. 10,925,709, and entitled "Systems and Methods for Transcatheter Aortic Valve Treatment" and claims priority to the following U.S. Provisional Patent Applications: (1) U.S. Provisional Patent Application Ser. No. 62/155,384, filed Apr. 30, 2015 and entitled "Systems and Methods for Transcatheter Aortic Valve Treatment"; and (2) U.S. Provisional Patent Application Ser. No. 62/210,919, filed Aug. 27, 2015 and entitled "Systems and Methods for Transcatheter Aortic Valve Treatment." The disclosures are each incorporated by reference herein in their entireties.

BACKGROUND

The present disclosure relates to methods and devices for replacing heart valves.

Patients with defective aortic heart valves are often candidates for a replacement heart valve procedure. The conventional treatment is the surgical replacement of the heart valve with a prosthetic valve. This surgery involves a gross thorocotomy or median sternotomy, cardiopulmonary bypass and cardiac arrest, surgical access and excision of the diseased heart valve, and replacement of the heart valve with a prosthetic mechanical or tissue valve. Valves implanted in this manner have historically provided good long term outcomes for these patients, with durability of up to ten or fifteen years for tissue valves, and even longer for mechanical valves. However, heart valve replacement surgery is highly invasive, can require lengthy recovery time, and is associated with short and long term complications. For high surgical risk or inoperable patients, this procedure may not be an option.

Recently, a minimally invasive approach to heart valve replacement has been developed. This approach, known as transcatheter aortic valve implantation (TAVI) or replacement (TAVR), relies on the development of a collapsible prosthetic valve which is mounted onto a catheter-based delivery system. This type of prosthesis can be inserted into the patient through a relatively small incision or vascular access site, and may be implanted on the beating heart without cardiac arrest. The advantages of this approach include less surgical trauma, faster recovery time, and lower complication rates. For high surgical risk or inoperable patients, this approach offers a good alternative to conventional surgery. Examples of this technology are the Sapien Transcatheter Valve (Edwards Lifesciences, Irvine, Calif.) and the CoreValve System (Medtronic, Minneapolis, Minn.). U.S. Pat. No. 6,454,799, which is incorporated herein by reference in its entirety, describes examples of this technology.

There are two main pathways for valves inserted using the TAVI approach. The first is a vascular approach via the femoral artery (referred to as a transfemoral approach), either percutaneously or through a surgical cut-down and arteriotomy of the femoral artery. Once placed into the femoral artery, the valve mounted on the delivery system is advanced in a retrograde manner (in the reverse direction as blood flow) up the descending aorta, around the aortic arch, and across the ascending aorta in order to be positioned across the native aortic valve. Transfemoral aortic valve delivery systems are typically over 90 cm in length and require the ability to navigate around the aortic arch. The relatively small diameter of the femoral artery and the frequent presence of atherosclerotic disease in the iliofemoral anatomy limits the maximum diameter of the delivery system to about 24 French (0.312") in diameter. The second pathway, termed transapical, involves accessing the left ventricle through the apex of the heart via a mini-thorocotomy, and advancing the valve delivery system in an antegrade fashion (in the same direction as blood flow) to the aortic valve position. This pathway is much shorter and straighter than the transfemoral path, but involves a surgical puncture and subsequent closure of the wall of the heart.

Other approaches have been described, including access from the subclavian artery, and direct puncture of the ascending aorta via a mini-thorocotomy. The subclavian approach (transsubclavian approach) has been used when the transfemoral route is contra-indicated, but may block flow to the cerebral vessel through the ipsilateral common carotid artery. A direct aortic puncture is usually considered if all other routes must be excluded due to anatomic difficulties including vascular disease. Puncture of the aortic wall, and subsequent closure, carries associated surgical risk including aortic dissection and rupture.

The transfemoral approach to the aortic valve, as opposed to the transapical or other alternative approaches, is a generally more familiar one to the medical community. Accessing the ascending aorta from the femoral artery is standard procedure for interventional cardiologists. Balloon valvuloplasty procedures via the transfemoral approach have been performed for years. The surgical approaches such as the transapical access or direct aortic puncture are less familiar and require practitioners with both surgical and endovascular skills; techniques for the surgical approaches are still evolving and whether they offer advantages over the transfemoral and transsubclavian methods have yet to be determined. However, problems also exist with the transfemoral and transsubclavian approaches. One is that the desired access vessel is often too small and/or is burdened with atherosclerotic disease, which precludes the artery as an access point. A second problem is that the pathway from the access point to the aortic valve usually involves one or more major turns of at least 90° with a relatively tight radii of curvature, 0.5" or less, requiring a certain degree of flexibility in the delivery system. This flexibility requirement restricts the design parameters of both the valve and the delivery system, and together with the required length of the delivery system reduces the level of control in accurately positioning the valve.

Both the transfemoral and transapical approaches have as potential complications the dislodgement of atherosclerotic and/or thrombotic debris, so-called "embolization" or the creation of "embolic debris," during access maneuvers, pre-dilation of the diseased valve, and implantation of the prosthetic valve. The most serious consequence of embolic debris is that it travels with the blood flow to the brain via one or more of the four primary conduits to the cerebral circulation, namely the right and left carotid arteries and the right and left vertebral arteries. Transfemoral TAVI procedures require passage of large device and delivery system components through the aortic arch and across the origins of the head and neck vessels that supply blood flow to the carotid and vertebral arteries, potentially loosening, fragmenting, and dislodging debris during its route to the aortic valve. The transapical TAVI procedure involves a puncture of the heart wall, which may generate embolic debris from the wall of the ventricle or ascending aorta, or may form thrombus or clot at the apical puncture location. During the vigourous motion of the beating heart, this clot can break free and travel to the brain as well. Both approaches require significant manipulation while the prosthetic valve is being placed: the TAVI implant and delivery system moves back and forth across the native aortic valve, potentially dislodging more debris from the diseased valve itself. With expansion of the valve implant, the native aortic valve is compressed and moved out of the stream of the cardiac output, another moment when the shearing and tearing of the native valve can free more debris to embolize to the brain.

Recently, there has been described an embolic filter protection device for use with TAVI procedures, as referenced in U.S. Pat. No. 8,460,335, which is incorporated herein by reference in its entirety. This device places a temporary screen over the ostium of the head and neck vessels to prevent passage of embolic particles while allowing blood flow into the vessels. While this device may offer some protection from larger embolic particles, it requires an additional vascular access and device deployment, adding to the cost and time of the procedure, and does not facilitate the passage of the prosthetic valve itself. Moreover, it does not provide protection during filter placement and retrieval; since the filter is deployed against the wall of the aorta, there is a high chance that the filter manipulation itself will be the cause of embolic complications.

SUMMARY

There is a need for an access system for endovascular prosthetic aortic valve implantation that provides a generally shorter and straighter access path than current systems and methods. This would allow the use of shorter and more rigid delivery systems which would offer a greater degree of control and easier placement of the aortic valve. There is also a need for an access system that provides protection from cerebral embolic complications during the procedure.

Disclosed herein are devices and methods that allow transcarotid or subclavian access via the common carotid artery to the native aortic valve, and transcatheter implantation of a prosthetic aortic valve into the heart or aorta. The devices and methods also provide means for embolic protection during such an endovascular aortic valve implantation procedure.

In one aspect, there is disclosed a system for aortic valve treatment, comprising: an arterial access sheath adapted to be introduced into an access site at the left common carotid artery, right common carotid artery, left subclavian artery, or right subclavian artery, wherein the arterial access sheath includes an internal lumen sized and shaped to receive a valve delivery system configured to deliver a prosthetic valve into the heart through the arterial access sheath; and an occlusion element on the arterial access sheath, the occlusion element adapted to occlude an artery.

In another aspect, there is disclosed a system for aortic valve treatment, comprising: an arterial access sheath adapted to be introduced into an access site at the left common carotid artery, right common carotid artery, left subclavian artery, or right subclavian artery, wherein the arterial access sheath has an internal lumen sized and shaped to receive a valve delivery system configured to deliver a prosthetic valve into the heart through the arterial access sheath; and a filter coupled to the arterial access sheath to provide embolic protection.

In another aspect, there is disclosed a system for transcarotid aortic valve treatment, comprising: an arterial access sheath adapted to be introduced into an access site at the left common carotid artery, right common carotid artery, left subclavian artery, or right subclavian artery, wherein the arterial access sheath has an internal lumen sized and shaped to receive a valve delivery system adapted to deliver a prosthetic valve into the heart through the arterial access sheath; and a return shunt fluidly connected to the arterial access sheath, wherein the shunt provides a pathway for blood to flow from the arterial access sheath to a return site.

In another aspect, there is disclosed a system for aortic valve treatment, comprising: an arterial access sheath adapted to be introduced into an access site at the left or right common carotid artery, or left or right subclavian artery, wherein the arterial access sheath has a first lumen sized and shaped to receive a valve delivery system configured to deliver a prosthetic valve into the heart through the arterial access sheath; a Y-arm disposed at a proximal region of the arterial access sheath; and a flow shunt fluidly connected to the Y-arm, wherein the flow shunt is adapted to perfuse the distal carotid artery.

In another aspect, there is disclosed a system for aortic valve treatment, comprising: an arterial access sheath adapted to be introduced into an access site at the left or right common carotid artery, or left or right subclavian artery, wherein the arterial access sheath has an internal lumen sized and shaped to receive a valve delivery system configured to deliver a prosthetic valve into the heart through the arterial access sheath; a side opening in the arterial access sheath adapted to allow blood flow antegrade into the tip of the access sheath and out the side opening to perfuse the distal carotid artery; and a dilator which is inside the access sheath during insertion of the access sheath into the artery and which prevents flow through the sheath and out the side opening during access sheath insertion.

In another aspect, there is disclosed a method of treating an aortic valve, comprising: forming a penetration at the neck of a patient in a wall of a common carotid artery; introducing an access sheath through the penetration; occluding the artery; inserting a guide wire through the access sheath and across the native aortic valve; and introducing a prosthetic valve through the access sheath and percutaneously deploying the prosthetic valve at or near the position of the native aortic valve.

In another aspect, there is disclosed a method of treating an aortic valve, comprising: forming a penetration at the neck of a patient in a wall of a common carotid artery; introducing an access sheath through the penetration; deploying a filter to provide embolic protection in an artery; inserting a guide wire through the access sheath and across the native aortic valve; and introducing a prosthetic valve through the access sheath and deploying the prosthetic valve at or near the position of the native aortic valve.

Other aspects, features and advantages should be apparent from the following description of various embodiments, which illustrate, by way of example, the principles of the disclosure.

BRIEF DESCRIPTION OF THE DRAWINGS

FIG. 1 shows a side view of an exemplary access sheath having an occlusion element mounted on the sheath.

FIG. 2 shows a side view of an exemplary access sheath having a filter element mounted on the sheath.

FIG. 3 shows a front view of the filter element.

FIGS. 4, 5A, and 5B show alternate embodiments of the access sheath.

DETAILED DESCRIPTION

Figure 6:
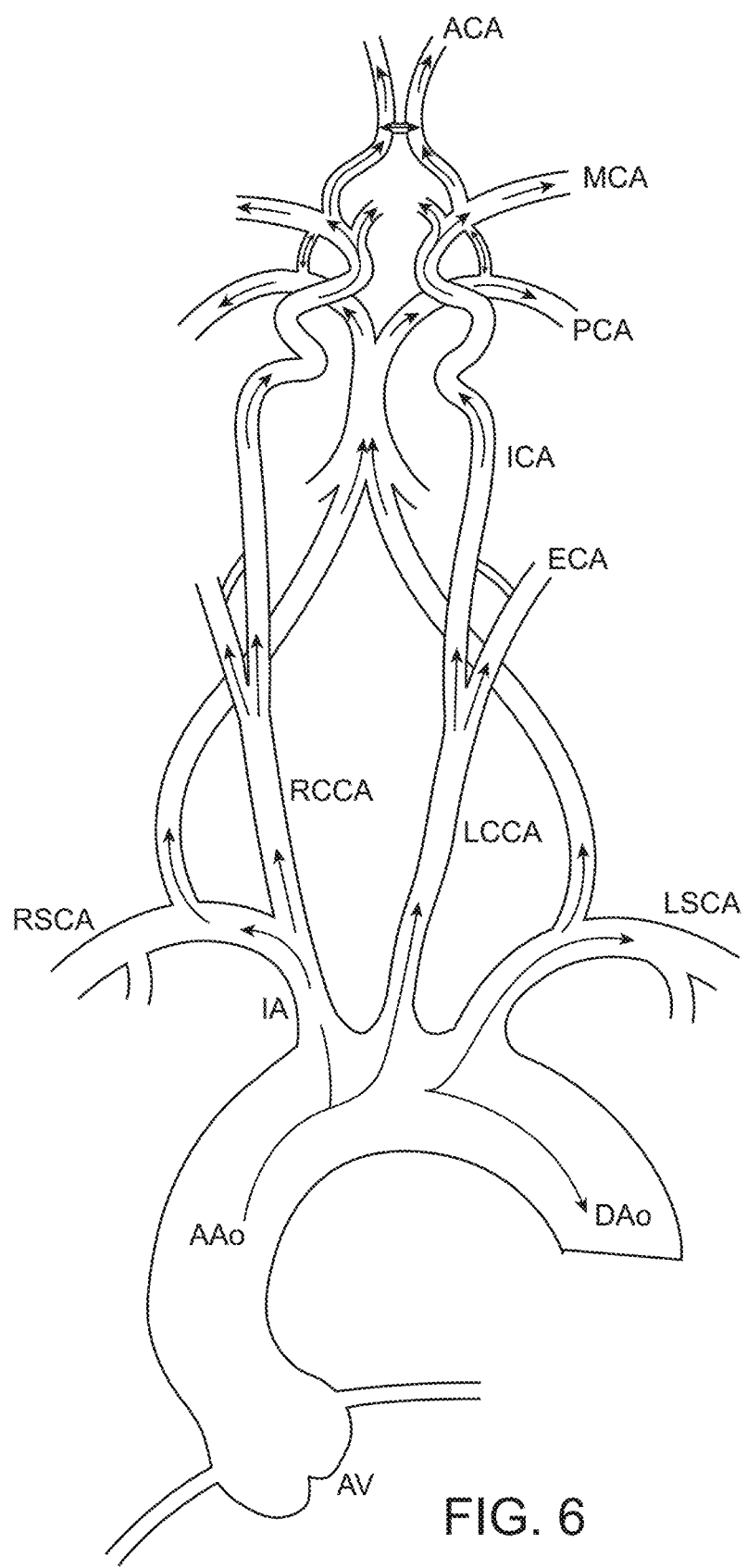
FIG. 6 schematically depicts a view of the vasculature showing normal circulation.

Disclosed herein are devices and methods that allow arterial access, such as transcarotid access via the common carotid artery, or subclavian access via the subclavian artery to the native aortic valve, and implantation of a prosthetic aortic valve into the heart or aorta. The devices and methods also provide means for embolic protection during such an endovascular aortic valve implantation procedure.

In an embodiment, transcarotid or subclavian access to the aortic valve is accomplished via either a percutaneous puncture or direct cut-down to the artery. A cut-down may be advantageous due to the difficulty of percutaneous vessel closure of larger arteriotomies in the common carotid artery. If desired, a pre-stitch may be placed at the arteriotomy site to facilitate closure at the conclusion of the procedure. An access sheath with associated dilator and guidewire is provided which is sized to fit into the common carotid or subclavian artery. The access sheath is inserted into the artery inferiorly towards the aortic arch. Either the left or the right common carotid or subclavian artery may be selected as the access site, based on factors including, for example, the disease state of the proximal artery and/or the aorta and the angle of entry of the carotid or innominate artery into the aorta. The carotid artery may then be occluded distal to the access site. If the access is via a direct surgical cut-down and arteriotomy, the occlusion may be accomplished via a vascular clamp, vessel loop, or Rummel tourniquet. Alternately, the access sheath itself may include an occlusion element adapted to occlude the artery, for example an occlusion balloon, to prevent embolic particulates from entering the carotid artery distal to the access site during the procedure.

FIG. 1 shows a side view of an exemplary arterial access sheath 110 formed of an elongate body having an internal lumen. In an embodiment, the sheath has a working length of 10-60 cm wherein the working length is the portion of the sheath that is insertable into the artery during use. The lumen of the sheath has an inner diameter large enough to accommodate insertion of an endovascular valve delivery system, such as an 18 French to 22 French (0.236" to 0.288") system. In an embodiment, the delivery system has an inner diameter as low as about 0.182" The access sheath 110 can have an expandable occlusion element 129 positioned on the access sheath. The occlusion element 129 is configured to be expanded to a size for occluding flow through the artery. The occlusion element 129 may be placed anywhere in the artery or aorta. In an embodiment, the occlusion element is an occlusion balloon.

Once the sheath 110 is positioned in the artery, the occlusion element 129 is expanded within the artery to occlude the artery and possibly anchor the sheath into position. The arterial access sheath 110 may include a Y-arm for delivery of contrast or saline flush, for aspiration, and/or may be fluidly connected to a shunt, wherein the shunt provides a shunt lumen or pathway for blood to flow from the arterial access sheath 110 to a return site such as a venous return site or a collection reservoir. In this regard, a retrograde or reverse blood flow state may be established in at least a portion of the artery. The sheath 110 may also include a Y-arm for inflation of the occlusion balloon via an inflation lumen, and a hemostasis valve for introduction of an endovascular valve delivery system into the sheath. Alternately, the sheath 110 may include an actuating element if the occlusion element is a mechanical occlusion structure. The endovascular valve delivery system may include a prosthetic valve and a delivery catheter. In an embodiment, the delivery catheter has a working length of 30, 40, 60, 70, or 80 cm.

In an embodiment, aspiration may be applied to the artery via the access sheath 110. In this regard, the access sheath 110 can be connected via a Y-arm 112 to an aspiration source, so that embolic debris may be captured which may otherwise enter the remaining head and neck vessels, or travel downstream to lodge into peripheral vessels. The aspiration source may be active, for example a cardiotomy suction source, a pump, or a syringe. Alternately, a passive flow condition may be established, for example, by fluidly connecting the Y-arm 112 to a shunt, which in turn is connected to a lower-pressure source such as a collection reservoir at atmospheric or negative pressure, or a venous return site in the patient. The passive flow rate may be regulated, for example, by controlling the restriction of the flow path in the shunt.

In an embodiment, the access system may be equipped with one or more embolic protection elements to provide embolic protection for one or both carotid arteries. For example, a filter may be included in the access system to provide embolic protection for one or both carotid arteries. In a variation of this embodiment, the filter is deployed via the contralateral carotid, brachial or subclavian artery, and positioned in the aortic arch across the ostium. If the sheath access site is the left common carotid artery, the filter may be positioned across the ostium of the innominate (also known as brachiocephalic) artery. If the sheath access site is the right common carotid artery, the filter may be positioned across the ostium of the left common carotid artery. In a variation of this embodiment, the filter is deployed across both the innominate and left common carotid artery, or across all three head and neck vessels (innominate artery, left common carotid artery, and left subclavian artery). The filter element may be built-in to the access sheath 110. Or, the filter element may be a separate element which is compatible with the access sheath 110. For example, the filter element may be a coaxial element which is slideably connected to the access sheath or an element which is placed side-by-side with the access sheath. The filter element may comprise an expandable frame, so that it may be inserted into the artery in a collapsed state, but then expanded at the target site to position the filter element across the opening of the artery or arteries.

FIG. 2 shows a side view of an exemplary access sheath 110 having a filter element 111 mounted on the sheath. FIG. 3 shows a front view of the filter element 111 showing an exemplary profile of the filter element 111. In the embodiment of FIG. 3, the filter element 111 is sized and shaped to fit within and block the head and neck vessels. In an embodiment, the deployed filter has a long dimension of about 2, 3, 4, or 5 cm and a short dimension of about 1, 1.5, or 2 cm. The profile shown in FIG. 3 is for example and it should be appreciated that the shape of the filter element 111 may vary. For example, the shape of the filter element may be oval, round, elliptical, or rectangular. The filter material may be woven or knitted textile material, or may be a perforated polymer membrane such as polyurethethane. The filter porosity may be 40, 100, 150, 200, or 300 microns, or any porosity in between. The expandable frame of the filter element may be made from spring material such as stainless steel or nitinol wire or ribbon.

In the embodiment with the filter element, occlusion and/or aspiration means may still be part of the system, to provide embolic protection during filter deployment before the valve implantation and filter retrieval after valve implantation. The filter element itself may be a primary method of embolic protection during the implantation procedure. The sheath 110 may also be equipped with both an occlusion element 129 and a filter element 111, as shown in FIG. 4.

In another variation of this embodiment, shown in FIG. 5A, the sheath 110 includes an aortic filter element 113 which is sized and shaped to be deployed across the ascending aorta and thus protect all the head and neck vessels from embolic debris. The shape of the filter element may vary. In an embodiment, the shape of the filter element may be a cone or a closed-end tube. The expandable frame of the filter frame is sized and shaped to traverse the entire diameter of the aorta when deployed. For example the expandable frame may be a loop which can expand from 12 to 30 mm in diameter. Alternately, the expandable frame may be a series of struts connected at one or both ends and which expand outwardly to deploy the filter element across the diameter of the aorta. The filter material may be woven or knitted textile material, or may be a perforated polymer membrane such as polyurethethane. The filter porosity may be about 40, 100, 150, 200, or 300 microns, or any porosity in between.

The expandable frame of the filter element may be made from spring material such as stainless steel or nitinol wire or ribbon. As with the previous variation, occlusion and aspiration means may be included in this variation to provide protection during filter deployment and filter retrieval. The aortic filter element 113 may be integral to the sheath, or be a separate device which is compatible with the sheath, for example may be coaxial or side-by-side with the access sheath. As shown in FIG. 5B, an embodiment of the sheath 110 may include both an aortic filter element 113 and an occlusion element 129.

FIG. 6 schematically depicts a view of the vasculature showing normal antegrade circulation. The blood vessels are labeled as follows in FIG. 6: ACA: anterior cerebral artery; MCA: middle cerebral artery; PCA: posterior cerebral artery; ICA: internal carotid artery; ECA: external carotid artery; LCCA: left common carotid artery; RCCA: right common carotid artery; LSCA: left subclavian artery; RSCA: right subclavian artery; IA: innominate artery; AAo: Ascending aorta; DAo: descending aorta; AV: aortic valve.

In certain situations, it may be desirable to provide a mechanism for perfusing the carotid artery upstream of the entry point of the access sheath 110 into the carotid or innominate artery. If the access sheath 110 is similar in size to the carotid or innominate artery, flow through the artery may be essentially blocked by the access sheath when the sheath is inserted into the artery. In this situation, the upstream cerebral vessels may not be adequately perfused due to blockage of the carotid artery by the sheath. In an embodiment of the access sheath 110, the sheath includes a mechanism to perfuse the upstream carotid and cerebral vessels.

Figure 7A:
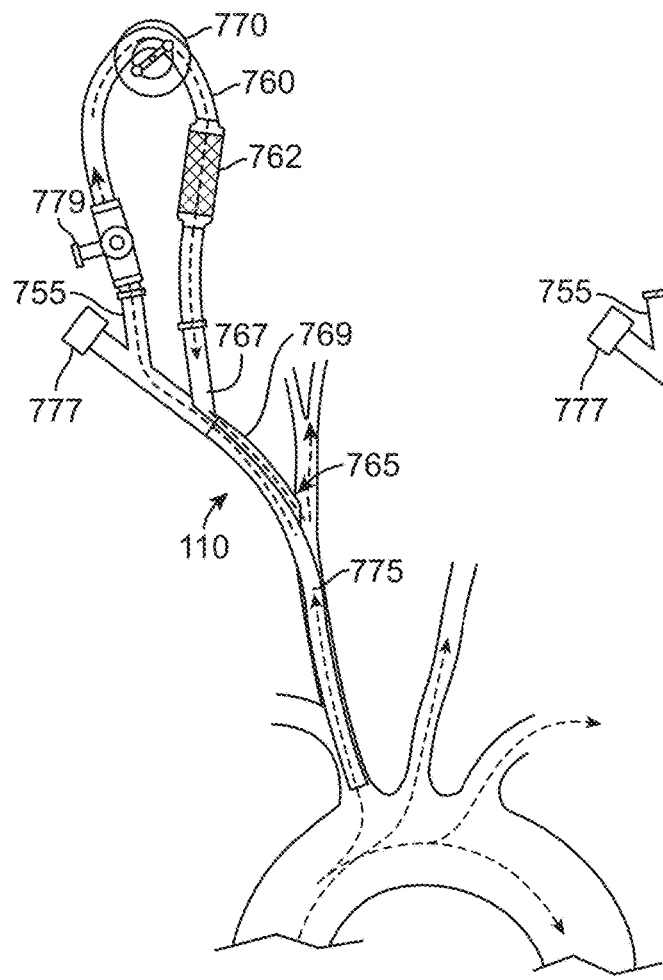
FIGS. 7A and 7B shows other embodiments of an access sheath deployed in the vasculature.

FIG. 7A shows an exemplary embodiment of such an access sheath 110 deployed in the vasculature. A proximal portion of the access sheath has two parallel, internal lumens that are part of a single monolithic structure of the access sheath. A first lumen 775 extends from the proximal end of the sheath to the distal tip of the sheath and is fluidly connected on the proximal end to a shunt Y-arm 755 and a hemostasis valve 777 located at the proximal end of the sheath. The first lumen 775 is sized and shaped to receive and enable delivery of a transcatheter aortic valve and delivery system via the hemostasis valve 777. For example, the first lumen has a length such that its distal opening is positioned at the heart or aorta. A second lumen 769 is positioned adjacent the first lumen and extends from the proximal end of the sheath to a distal opening at a location mid-shaft 765 and is fluidly connected on the proximal end to a second, perfusion Y-arm 767. There is an opening on the distal end of the second lumen at the location 765. The second lumen 769 is sized and shaped to enable shunting of blood to the carotid artery distal of the access sheath insertion site. A radiopaque shaft marker may be positioned on the sheath at this location to facilitate visualization of this opening to the user under fluoroscopy. The perfusion lumen has a length such that the distal opening of the perfusion lumen can be positioned in and perfuse a distal carotid artery when in use. The proximal end of the first lumen has a proximal connector with the hemostasis valve 777 and a Y-arm. As mentioned, the hemostasis valve is sized to fit therethrough an arterial valve delivery system. The proximal end of the perfusion lumen also has a proximal connector. The proximal connectors and/or Y-arms permit a shunt to be attached.

The Y-arm 755 is removably connected to a flow shunt 760 which in turn is removably connected to the second Y-arm 767. The shunt defines an internal shunt lumen that fluidly connects the first lumen 775 to the second lumen 769. A stopcock 779 may be positioned between the Y-arm 755 and the flow shunt 760 to allow flushing and contrast injection while the shunt 760 is connected. When the sheath is positioned in the artery, arterial pressure drives blood flow into the distal end of the first lumen 775 of the arterial access sheath, out the first lumen from Y-arm 755, then into the shunt 760, and back into the sheath via the Y-arm 767. The blood then flows into the parallel lumen 769 and into the distal carotid artery at the location 765 to perfuse the vasculature distal of the arterial sheath 110. An in-line filter element 762 may be included in the flow shunt 760 so that emboli generated during the procedure are not perfused into the cerebral artery. In the event the sheath 110, shunt 760, and lumen 769 create a flow restriction that limits adequate perfusion, the flow shunt 760 may incorporate an active pump 770 to drive blood flow and provide the required level of cerebral perfusion. This may be especially true when the valve is being delivered through the first lumen 775 of the access sheath 110.

Figure 7B:
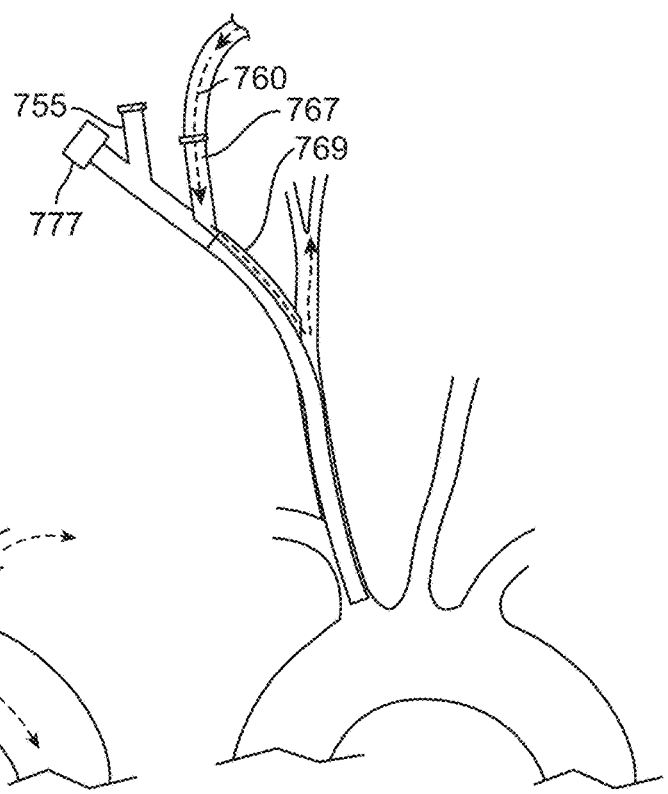

FIG. 7B shows a variation of the embodiment of FIG. 7A. The Y-arm 767 fluidly connects the shunt 760 to the parallel lumen 769 that re-introduces blood from the shunt 760 into the artery at location 765 when positioned in the artery. The shunt 760 in this embodiment is not fluidly connected to the first lumen 775 in the sheath. The shunt 760 rather than receiving blood from the access sheath via Y-arm 755 may be connected to another arterial blood source via a second sheath, for example a femoral or subclavian artery or the contralateral carotid artery. In this variation, the shunted blood flow is not restricted by the delivery of the valve through the first lumen 775 of the access sheath. In this embodiment, there is no need for a filter 762 in the shunt line, as the blood source is far from the treatment area and there is minimal risk of distal emboli in the shunted blood. The Y-arm 755 may still be used for flushing and contrast injection into the sheath. In another variation, shown in FIG. 8A, the arterial access sheath 110 has a single lumen 775 which is fluidly connected to a Y-arm 755 at the proximal region. The lumen 775 is sized and shaped to receive and enable delivery of a transcatheter aortic valve and delivery system via a hemostasis valve 777. The Y-arm 755 is connected to a flow shunt 760 which in turn is connected to a second arterial sheath 802 which is sized and shaped to be introduced into the carotid artery distal to arterial access point where the access sheath 110 is introduced. A stopcock 779 may be positioned between the Y-arm 755 and the flow shunt 760 to allow flushing and contrast injection while the shunt 760 is connected. When the sheath is properly positioned in the artery, the arterial pressure drives flow into the lumen 775 of the sheath 110, out the first lumen via Y-arm 755, then through the shunt 760, through the second catheter 802, and back into the carotid artery upstream from the arterial access point to perfuse the vasculature distal of the arterial sheath 110. As above, a filter element 762 may be included in the flow shunt 760 so that emboli generated during the procedure are not perfused into the cerebral artery. In the event the sheath 110 and shunt 760 experience flow restriction that limits adequate perfusion, for example when the valve is being delivered through the lumen 775 of the access sheath 110, the flow shunt may incorporate an active pump 770 to drive blood flow and provide the required level of cerebral perfusion.

Figures 8A, 8B:
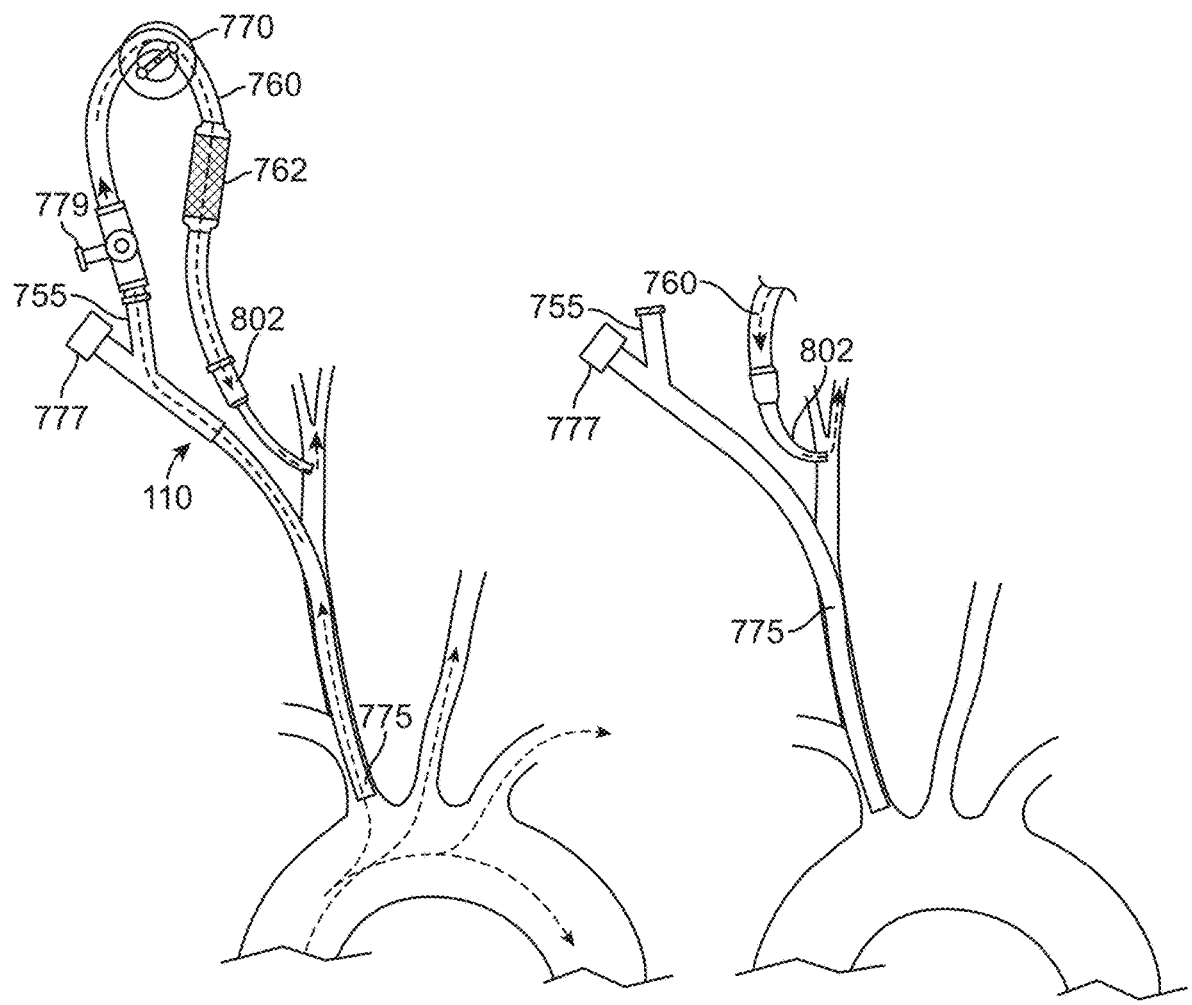
FIGS. 8A and 8B shows other embodiments of an access sheath deployed in the vasculature.

FIG. 8B shows a variation of the embodiment of FIG. 8A. Here, the second arterial sheath 802 is removably or fixedly connected to a shunt or flow line 760 which in turn is connected to another arterial source via another sheath, for example a femoral or subclavian artery or the contralateral carotid artery. In this variation, the shunted blood flow is not restricted by the delivery of the valve through the lumen 775 of the access sheath. In this embodiment, there is no need for a filter 762 in the shunt line, as the blood source is far from the treatment area and there is minimal risk of distal emboli in the shunted blood. The Y-arm 755 may still be used for flushing and contrast injection into the sheath.

In the embodiments described above in FIGS. 7A and 7B and FIGS. 8A and 8B, the arterial access sheath 110 may include an occlusion element (not shown) at the distal end of the sheath, configured to occlude the carotid artery and to assist in prevention of emboli from entering the carotid artery. Additionally, in these embodiments, the flow shunt 760, and if applicable pump 770 and/or the second sheath 820 may be provided as separate components in a single kit to enable transcarotid access and carotid shunting during a catheter-based aortic valve replacement procedure.

Although the figures show sheath insertion in the common carotid artery, a similar sheath or sheath/shunt systems may be designed for sub-clavian access.

Figure 9:
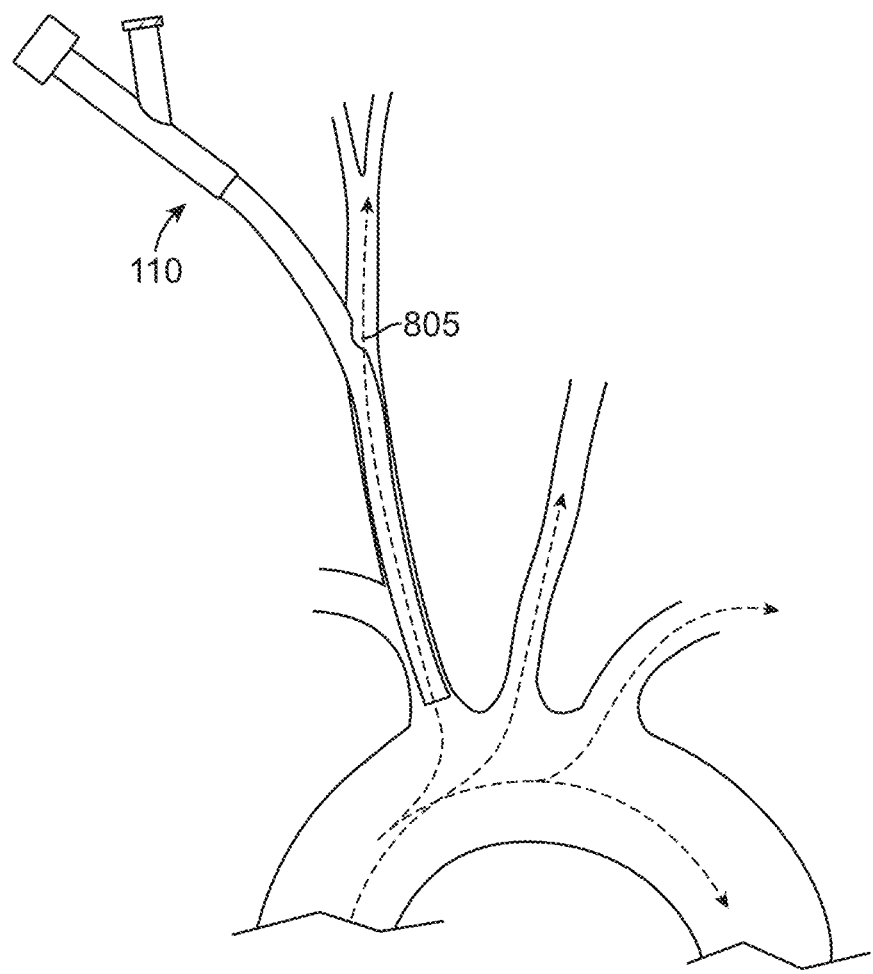
FIG. 9 shows another embodiment of an access sheath deployed in the vasculature.
Figure 10:
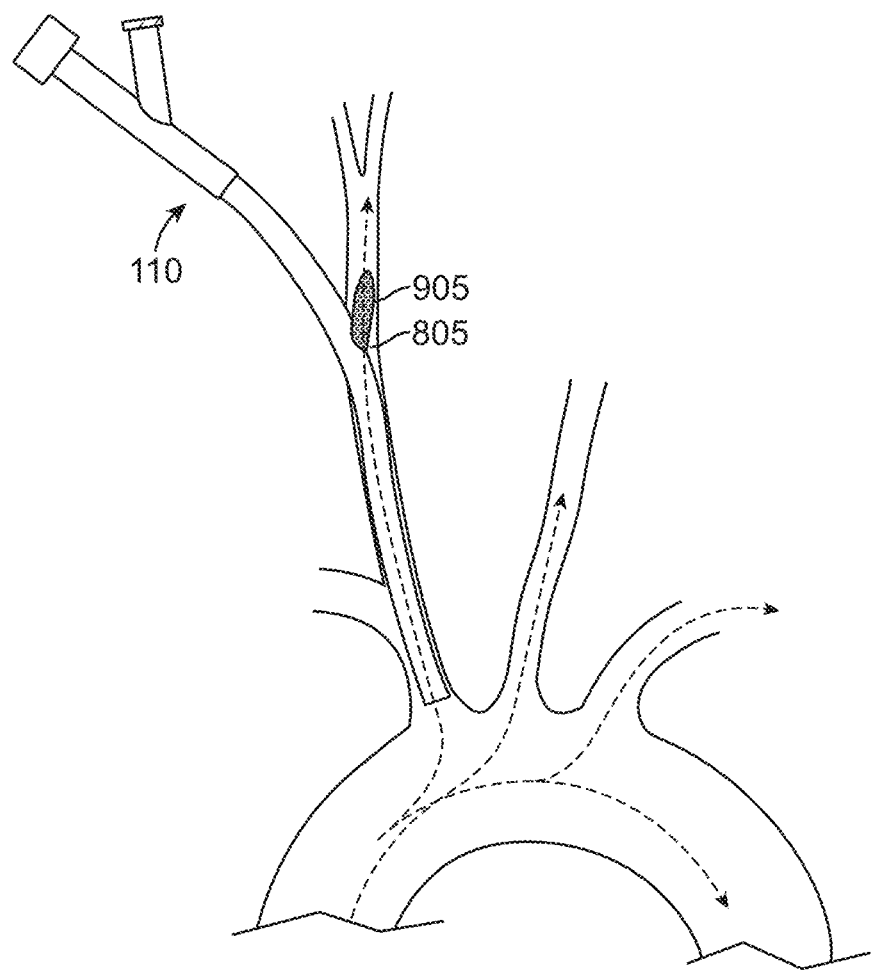
FIG. 10 shows another embodiment of an access sheath deployed in the vasculature.

In another embodiment, the access sheath 110 may have at least one side opening 805 located between the distal end and the proximal end of the sheath 110, as shown in FIG. 9. A dilator may be positioned inside the sheath 110 to block the side opening 805 during insertion of the sheath. The dilator is used to aid in sheath insertion into the artery. When the access sheath 110 is inserted into the artery and the dilator is removed, the dilator no longer blocks the opening 805 so that blood may flow out of the access sheath 110 through the side opening 805 into the distal carotid artery. During introduction of the endovascular valve delivery system through the access sheath 110 and into the artery, the delivery system may restrict the flow through the sheath and artery and may reduce the level of cerebral perfusion. However, this period of the procedure is transient, and reduction of cerebral perfusion during this limited period of time should not present a clinical issue. In a variation of this embodiment as shown in FIG. 10, the side opening 805 may have a filter 905 that covers the opening 805. The filter 905 is configured to capture embolic debris so that the debris does not pass downstream towards the cerebral arteries. The filter 905 may be sized and shaped to bulge out of the sheath 110, so that when the endovascular valve is inserted into the sheath 110, the debris is not pushed forward and out the distal end of the sheath into the artery. In an embodiment, the filter is very thin, perforated film or woven material, similar in composition to embolic distal filter materials. Filter porosity may be about 150, 200, or 250 microns. Though FIGS. 9 and 10 show sheath insertion in the common carotid artery, a similar sheath may be designed for sub-clavian access, in which the sheath insertion site is farther from the carotid artery and the side opening may be placed correspondingly further towards the tip of the sheath.

The sheath in embodiments shown in FIGS. 7-10 may optionally include a positioning element which can be deployed once the sheath is inserted into the blood vessel. The positioning element can be used to position the sheath in the vessel such that the side opening 805 remains in a desired location inside the vessel. This positioning feature may take the form of a deployable protruding member such as a loop, braid, arm, or other protruding feature. This feature may be retracted during sheath insertion into the artery but deployed after the sheath is inserted and the opening is inside the vessel wall. Sheath retention may also be achieved, for example, by an eyelet or other feature in the Y-arm of the access sheath 110 which allows the sheath to be secured to the patient once positioned correctly.

An exemplary valve and delivery system which has been configured to be delivered through the transcarotid access sheath 110 is shown in FIG. 20. The route from the transcarotid access site is fairly short and straight, as compared to the transfemoral or subclavian approach. As a result, the delivery system can be shorter and the proximal section can be quite rigid, both of which will allow greater push and torque control resulting in increased accuracy in positioning and deploying the prosthetic valve. The distal section has increased flexibility to allow accurate tracking around the ascending aorta and into position at the aortic annulus. Materials for the delivery system may include reinforced, higher durometer, and/or thicker walled materials as compared to current delivery systems to provide this increased rigidity.

The balloon expandable prosthetic aortic valve 205 is mounted on the distal end of an endovascular valve delivery system 200. The delivery system has a distal tapered tip 220 and an expandable balloon 215 on the distal end of an inner shaft 210. In an embodiment, the system also has an outer sleeve, such as for example a pusher sleeve 230, that is slidable along the long axis of the device and which maintains the valve in position on the balloon during delivery. A proximal control assembly contains a mechanism for retracting the pusher sleeve, such as a sliding button 270 on a proximal handle 240. In FIG. 20, the pusher sleeve 230 is shown retracted from the valve and proximal balloon so that the valve can be expanded without interference from the pusher sleeve 230. A connector 250 allows connection of an inflation device to the balloon inflation lumen of the balloon 215. A proximal rotating hemostasis valve 260 allows system flushing as well as sealing around a guidewire (not shown) as the valve delivery system is being advanced over the guidewire and into position.

The working length of the valve delivery system is configured to allow delivery of the valve to the aortic annulus from a transcarotid access site. Specifically, the working length of the valve delivery system 200 is between 45 and 60 cm. The delivery system shaft is also configured for delivery from a right or left carotid access site. Specifically, the shaft has a proximal stiff section 280 and a more flexible distal section 290. In an embodiment, the distal section is 2 to 4 times more flexible than the proximal stiff section. In an embodiment, the distal flexible section is between one quarter to one third the total working length of the valve delivery system. Specifically, the distal flexible section is in the range 10 cm to 20 cm. In an alternate embodiment, the valve delivery system has a transition section of one or more flexible lengths which fall between the flexibility of the distal flexible section and the proximal flexible section.

Figure 21:
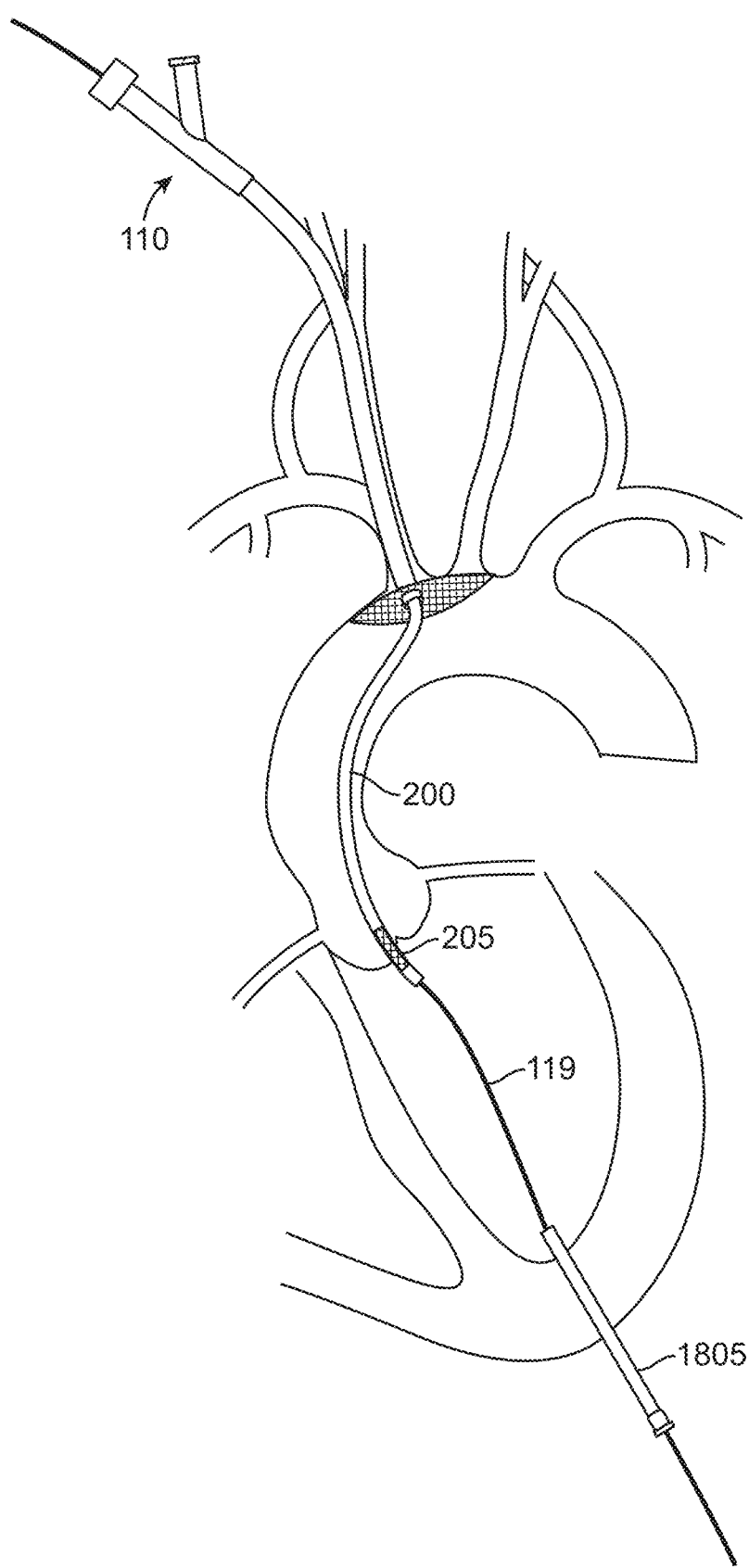
FIG. 21 shows another embodiment for delivering a prosthetic valve.
Figure 22:
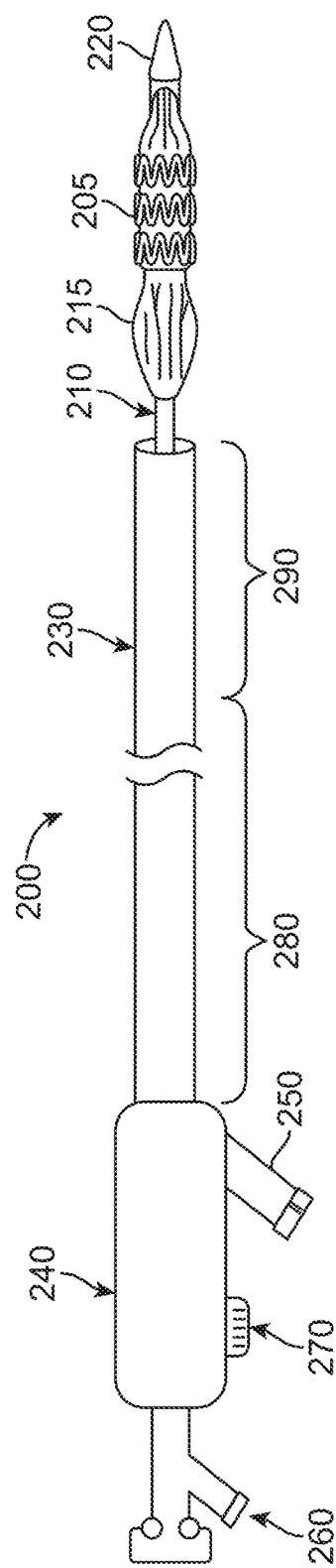
FIG. 22 shows an embodiment of a transcarotid prosthetic aortic valve and delivery system.
Figure 23:
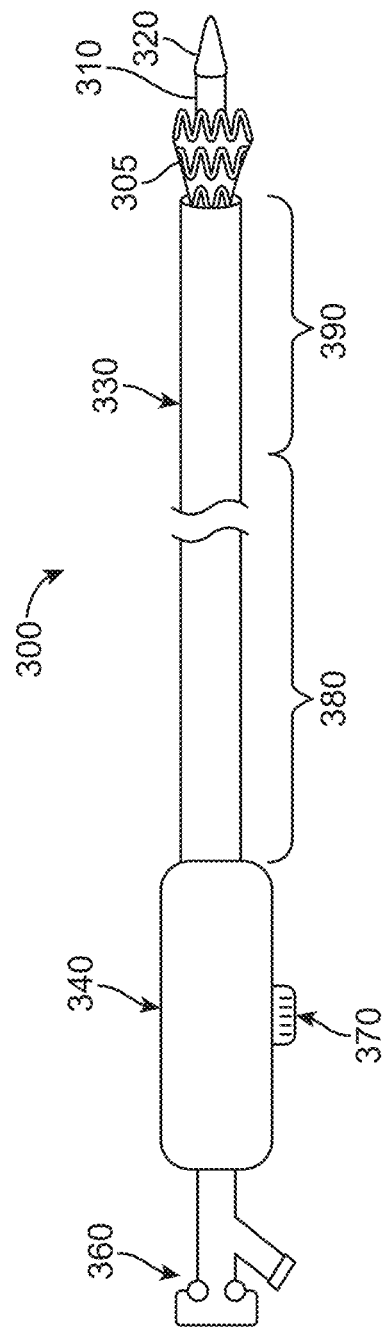
FIG. 23 shows an alternate embodiment of a transcarotid prosthetic aortic valve and delivery system.

Another exemplary valve and delivery system configured for transcarotid delivery is shown in FIG. 21. The self-expanding prosthetic aortic valve 305 is mounted on the distal end of an endovascular valve delivery system 300. The delivery system has a distal tapered tip 320 on the distal end of an inner shaft 310. The valve 305 is positioned on the inner shaft 310 and contained in a retractable sleeve 330 that can slide along the longitudinal axis of the device. A proximal control assembly contains a mechanism for retracting the retractable sleeve, such as a sliding button 370. In an embodiment, the design of the valve 305 and sleeve 330 are such that the sleeve can be readvanced in a distal direction to abut and to collapse the valve so that the valve 305 can be re-positioned if the first position was inaccurate. A proximal rotating hemostasis valve 360 allows system flushing as well as sealing around a guidewire (not shown) as the valve delivery system is being advanced over the guidewire and into position.

As with the previous embodiment, the working length of the valve delivery system is configured to allow delivery of the valve to the aortic annulus from a transcarotid access site. Specifically, the working length of the valve delivery system 300 is between 45 and 60 cm. The delivery system shaft is also configured for delivery from a right or left carotid access site. Specifically, the shaft has a proximal stiff section 380 and a more flexible distal section 390. In an embodiment, the distal section is 2 to 4 times more flexible than the proximal stiff section. In an embodiment, the distal flexible section is between one quarter to one third the total working length of the valve delivery system. Specifically, the distal flexible section is in the range 10 cm to 20 cm. In an alternate embodiment, the valve delivery system has a transition section of one or more flexible lengths which fall between the flexibility of the distal flexible section and the proximal flexible section.

Exemplary methods of use are now described. In an embodiment, a general method includes the steps of forming a penetration from the neck of a patient into a wall of a common carotid artery; introducing an access sheath through the penetration with the tip directed inferiorly towards the ostium of the artery; inserting a guide wire through the access sheath into the ascending aorta and across the native aortic valve; and introducing a prosthetic valve through the access sheath and percutaneously deploying the prosthetic valve at or near the position of the native aortic valve. In an embodiment, the artery is occluded distal (upstream) from the tip of the sheath.

Figure 11:
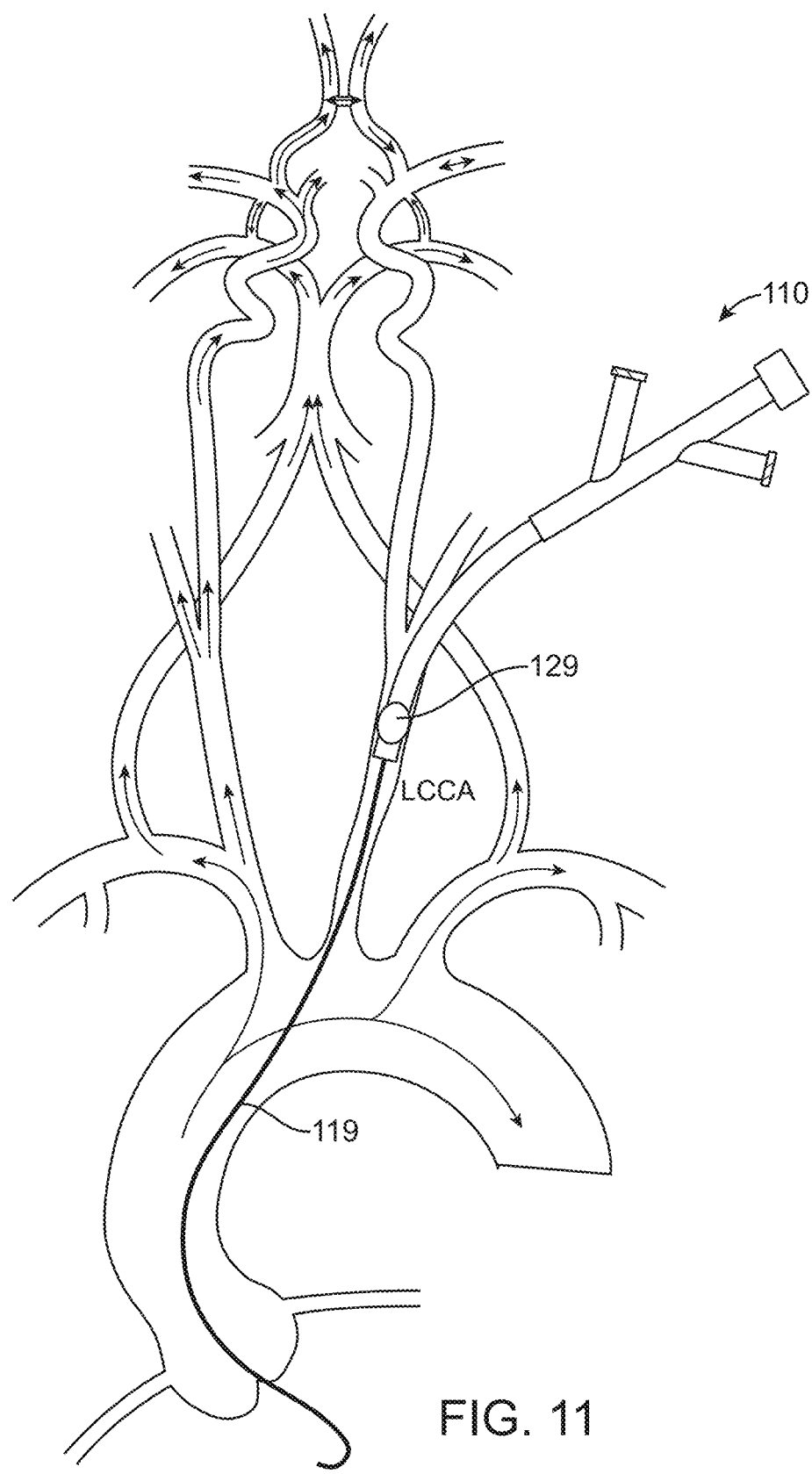
FIG. 11 shows another embodiment of an access sheath deployed in the vasculature with an occlusion element occluding the left common carotid artery.
Figure 12:
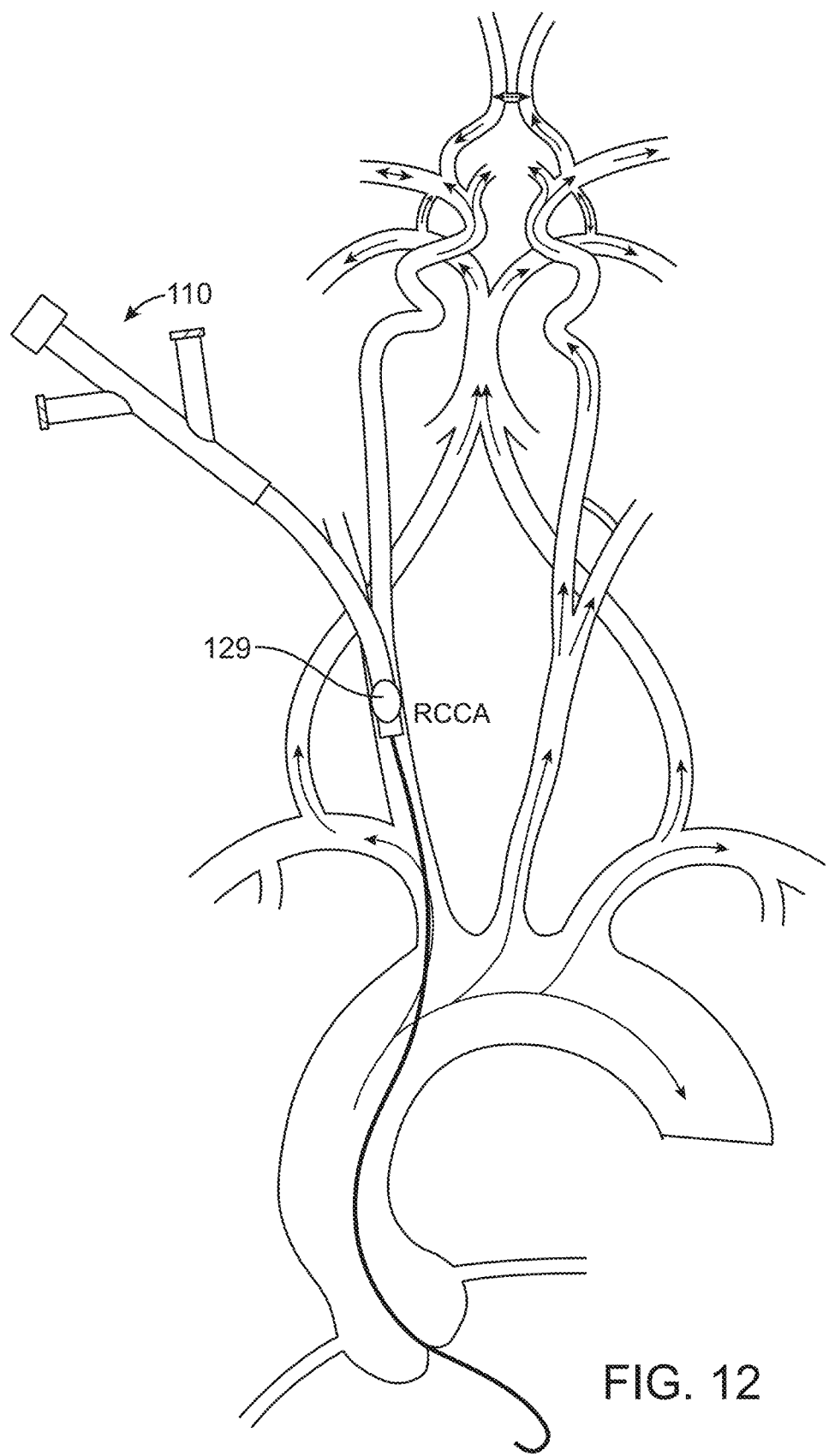
FIG. 12 shows another embodiment of an access sheath deployed in the vasculature with an occlusion element occluding the right common carotid artery.
Figure 13:
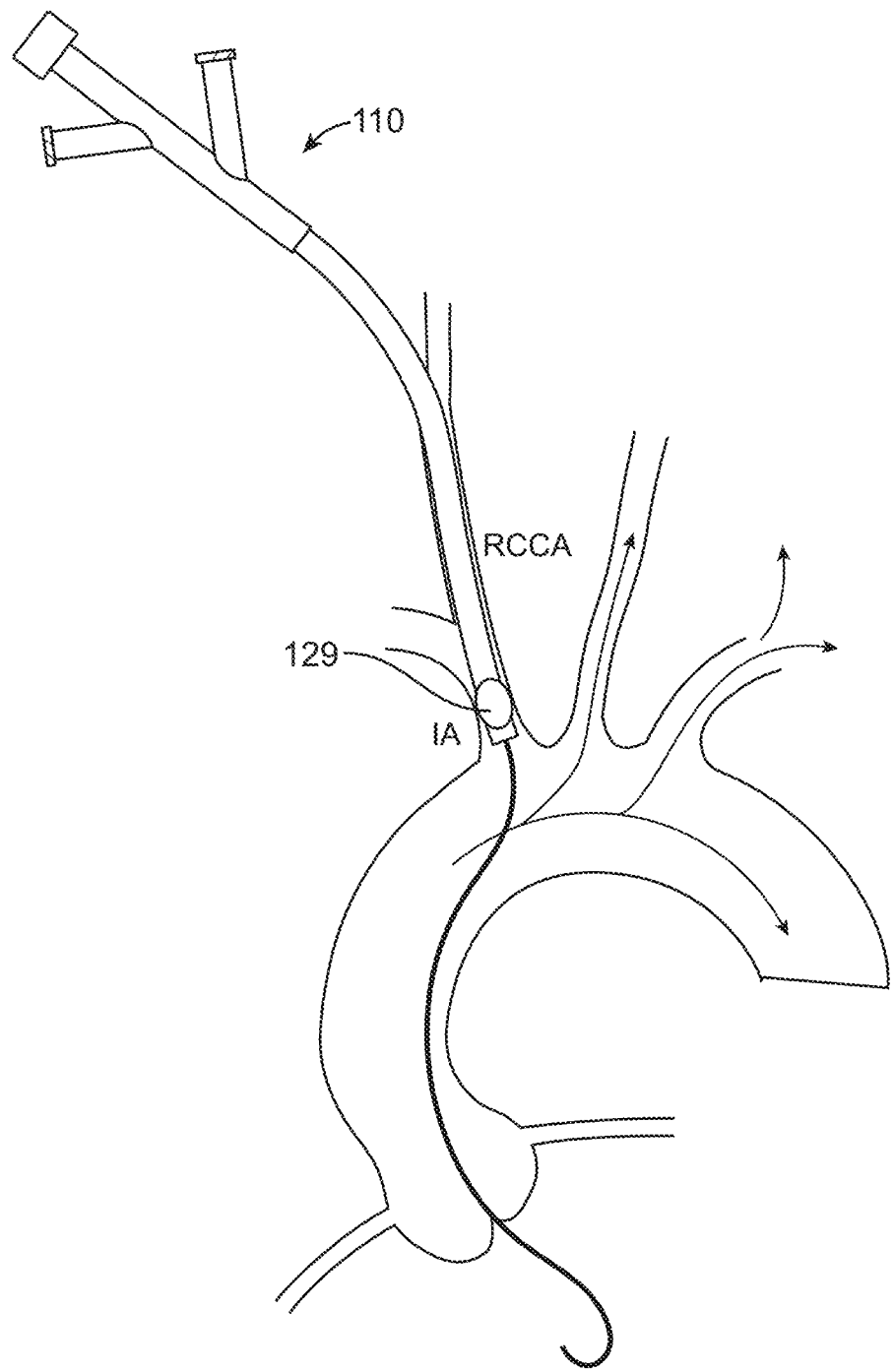
FIG. 13 shows another embodiment of an access sheath deployed in the vasculature with an occlusion element occluding the innominate artery.

In particular, the access sheath 110 is first inserted into the vasculature such as via either a percutaneous puncture or direct surgical cut-down and puncture of the carotid artery. As mentioned, a transcarotid approach to the aortic valve may be achieved via the LCCA. Once properly positioned, the occlusion element 129 may be expanded to occlude the LCCA, as shown in FIG. 11. In another embodiment, a transcarotid approach to the aortic valve may be achieved via the RCCA, with the occlusion element 129 occluding the RCCA, as shown in FIG. 12. In another embodiment, a transcarotid approach to the aortic valve may be achieved via the RCCA, with the occlusion element 129 occluding the innominate artery IA, as shown in FIG. 13. The occlusion achieved via the occlusion element 129 can also be achieved via direct clamping of the carotid vessel, e.g. with a vascular clamp, vessel loop or Rummel tourniquet.

Once the access sheath is positioned and the embolic protection means are deployed via occlusion, aspiration, and/or filter elements, access to the aortic valve is obtained via a guidewire 119 (such as a 0.035" or 0.038" guidewire) inserted into the sheath 110 and directed inferiorly into the ascending aorta and across the native aortic valve. Pre-dilation of the native aortic valve can be performed with an appropriately sized dilation balloon, for example a valvuloplasty balloon, before valve implantation. The guidewire 119 is used to position a balloon across the valve and the balloon is inflated, deflated, and then removed while the guidewire remains in place.

Figure 14:
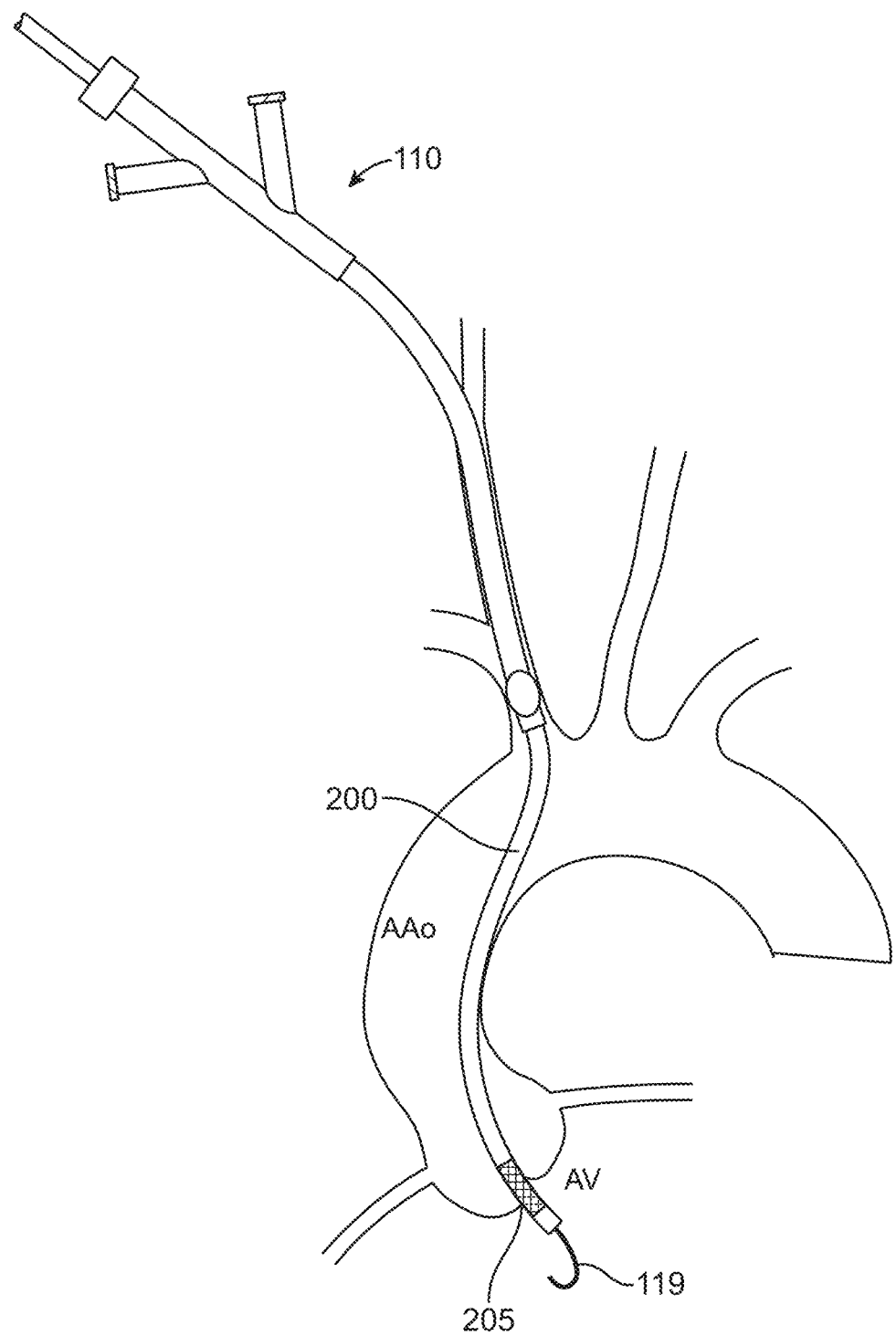
FIG. 14 shows a delivery system deploying an endovascular prosthetic valve via an access sheath 110 and guidewire 119.

An endovascular prosthetic valve 205 and delivery system 200 is then inserted through the access sheath 110 over the guidewire 119 and the valve 205 positioned at the site of the native aortic valve (as shown in FIG. 14). The prosthetic valve 205 is then implanted. At the conclusion of the implantation step, the implanted prosthetic valve 205 function can be accessed via ultrasound, contrast injection under fluoroscopy, or other imaging means. Depending on the design of the delivery system 200, the prosthetic valve 205 may be adjusted as needed to achieve optimal valve function and position before final deployment. The delivery system 200 and guidewire 119 are then removed from the access sheath 110. After removal of the delivery system 200 and guidewire 119, the embolic protection elements are removed. Aspiration may continue during this time to capture any embolic debris caught in the sheath tip, occlusion element and/or filter elements.

The access sheath 110 is then removed and the access site is closed. If the access was a surgical cutdown direct puncture, the vessel is closed either via tying off the pre-placed stitch or with manual suturing or with a surgical vascular closure device, as described in more detail below. If the access was percutaneous, percutaneous closure methods and devices may be employed to achieve hemostasis at the access site. In an embodiment, the closure device is applied at the site of the penetration before introducing the arterial access sheath through the penetration. The type of closure device can vary.

The access site described above is either the left or right common carotid artery. Other access sites are also possible, for example the left or right subclavian artery or left or right brachial artery. These arteries may require longer and/or more tortuous pathways to the aortic valve but may offer other advantages over a carotid artery access, for example the ability to work away from the patient's head, the ability to avoid hostile neck anatomy such as previous carotid endarterectomy or other cervical surgery or radiation, or less risky in case of access site complication. In addition, carotid artery disease, or small carotid arteries may preclude common carotid artery access. In the case of any of these access sites, occlusion, aspiration, and/or filtering the head and neck vessels during TAVI may increase the speed and accuracy of the procedure, and decrease the rate of embolic complications.

Figure 15C:
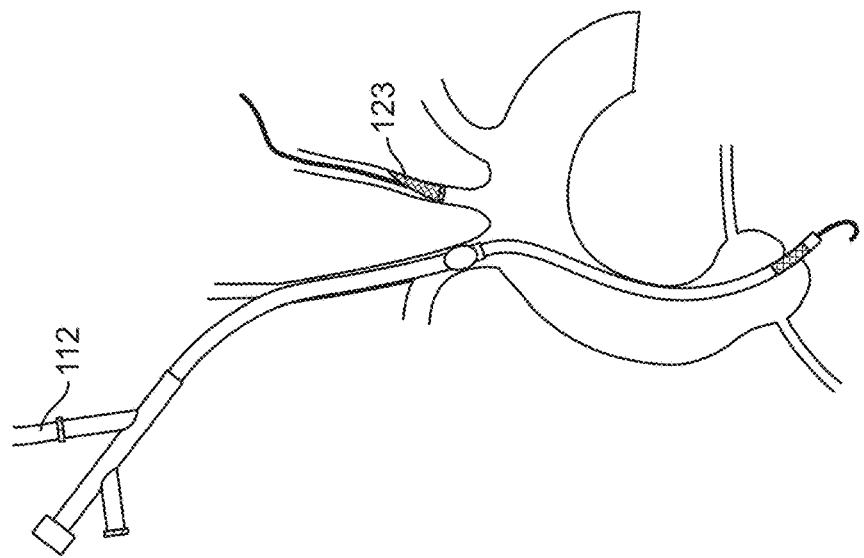
FIG. 15C shows an alternate embodiment wherein the filter is sized and shaped to be deployed in the artery distal to the ostium of the artery.
Figure 15B:
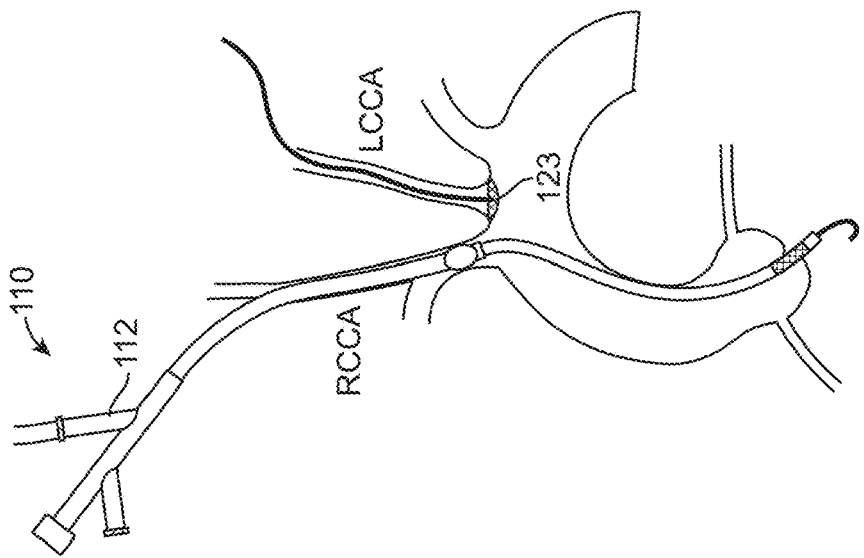
FIGS. 15A-15B show embodiments wherein a filter is sized and shaped to be deployed across the ostium of the artery.
Figure 15A:
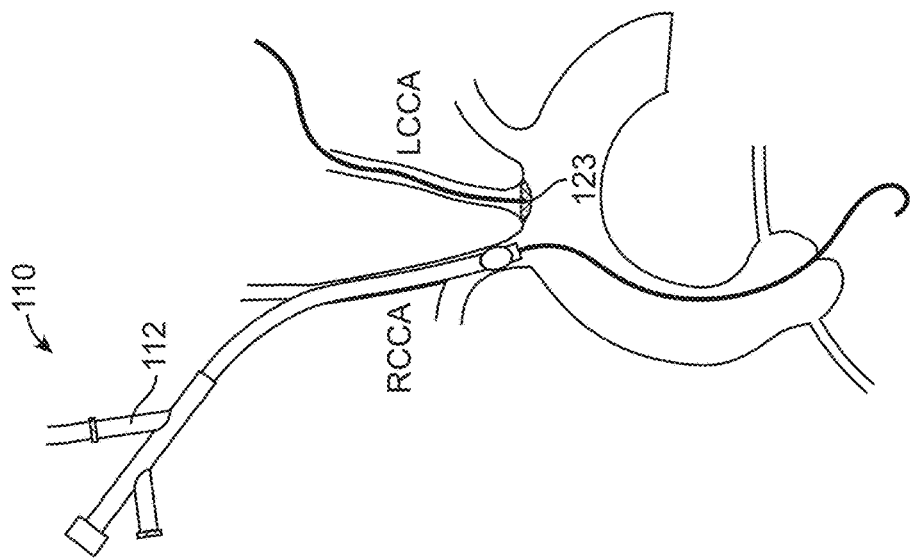

Various forms of embolic protection were described above including occlusion elements and filters. Additional embodiments that incorporate filters as means of embolic protection for all the head and neck vessels are now described. FIGS. 15A and 15B show embodiments wherein a filter 123 is sized and shaped to be deployed across the ostium of the artery contralateral (on the opposite side) to the carotid artery being accessed (left carotid artery if the right carotid artery is accessed, or innominate artery if the left carotid artery is accessed.) FIG. 15C shows an alternate embodiment, wherein the filter 123 is sized and shaped to be deployed in the artery distal to the ostium of the artery. The filter 123 can be placed via the contralateral carotid access site, or via a brachial or subclavian artery access site. Blood flow may proceed antegrade through the filter into the contralateral artery, while preventing the flow of embolic particles to the head and neck circulation.

Figure 16A:
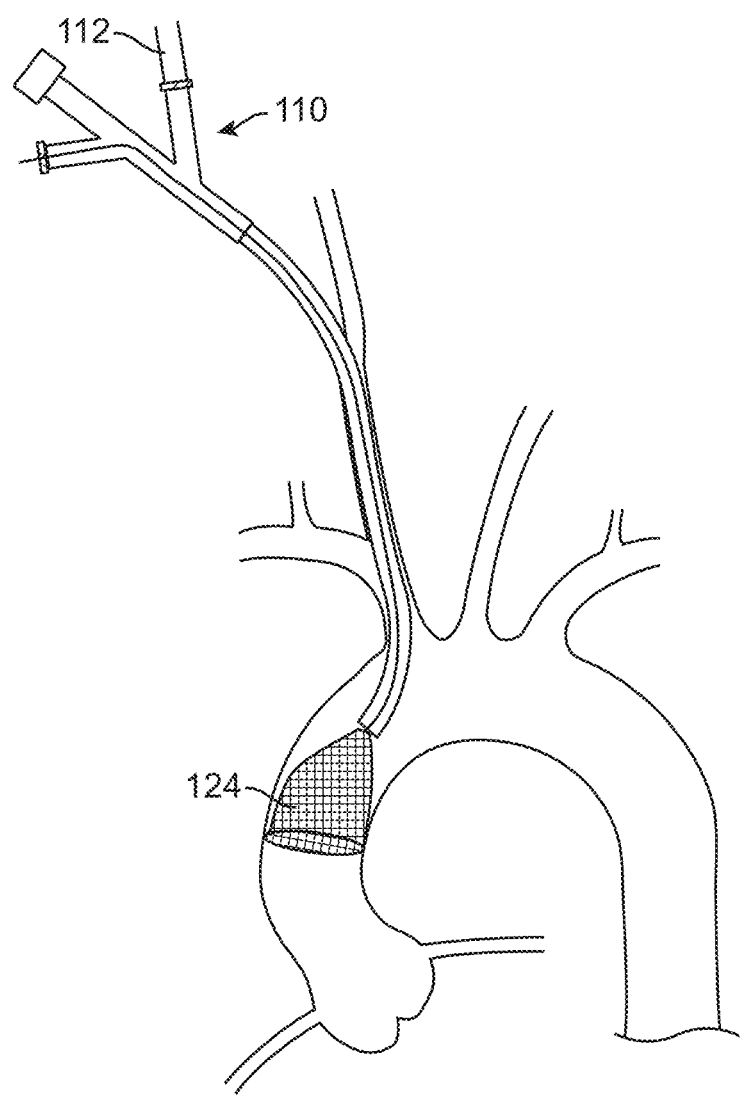
FIGS. 16A, 16B, and 16C show embodiments wherein the filter is delivered through the access sheath.
Figure 16B:
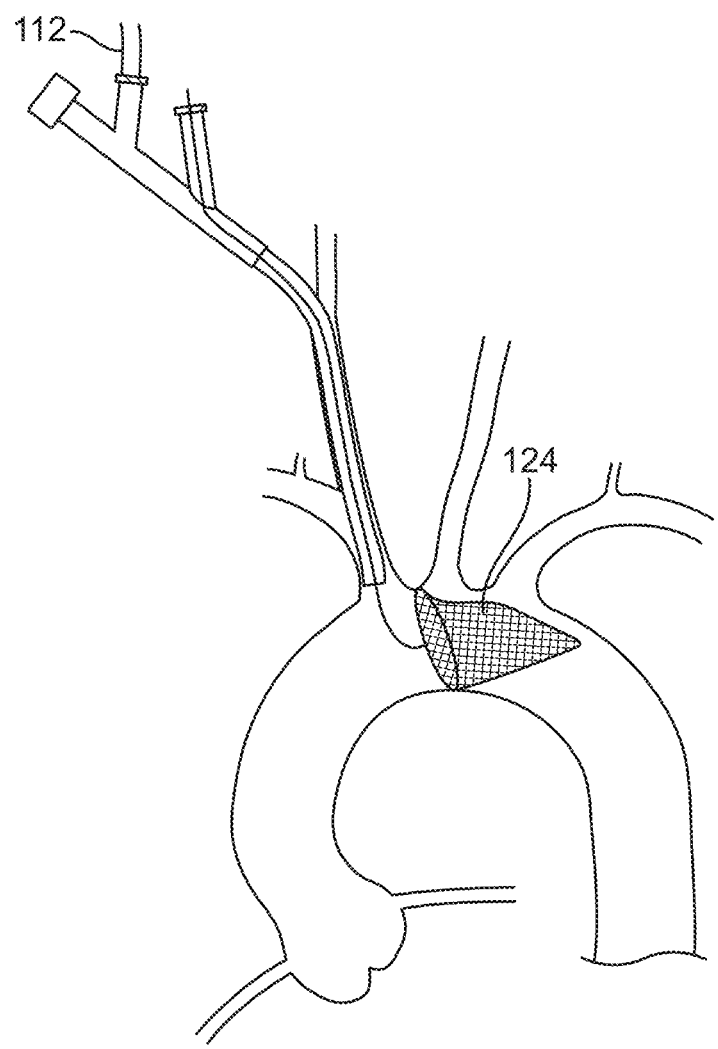
Figure 16C:
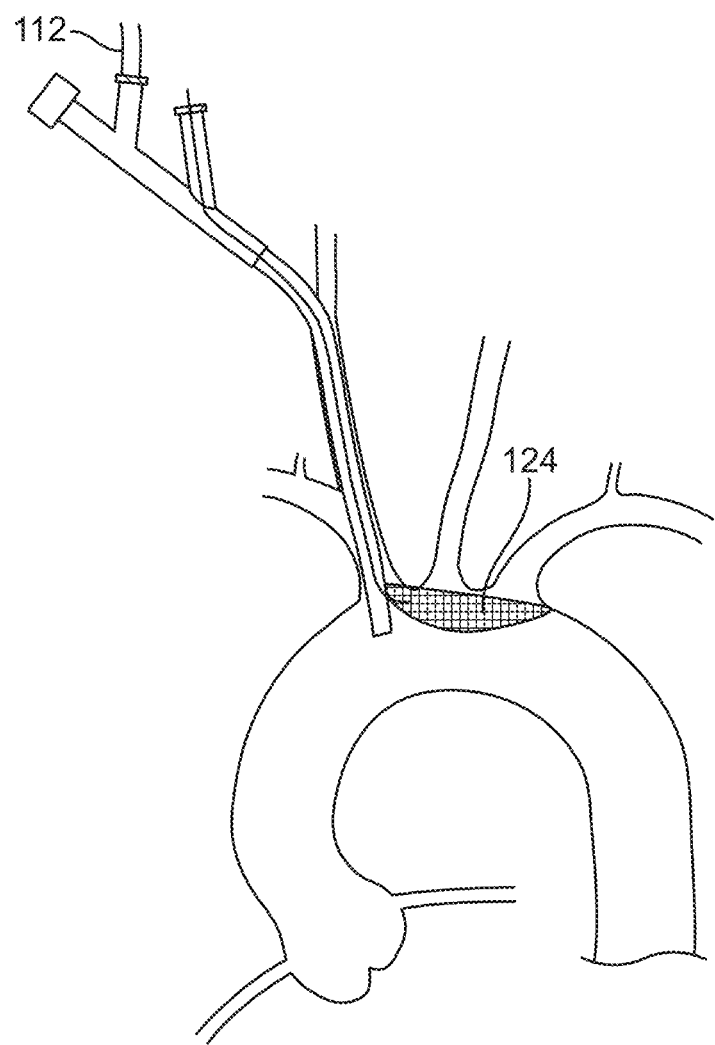

FIGS. 16A, 16B, and 16C show alternate embodiments wherein a filter is sized and shaped to be delivered through a lumen of the access sheath 110, either the main lumen or a separate lumen. In FIG. 16A, the filter 124 is sized and shaped to be deployed in the ascending aorta. In this embodiment, the valve is delivered through the filter material and into the aortic valve position. The filter may have a pre-formed slit or opening to allow the passage of the valve through the filter. The pre-formed slit(s) can be formed on the filter material to allow the passage of the valve though the filter while minimizing the size of the hole(s) created from the slit. For example the pattern of the slit(s) to create a one-way valve where the valve system can pass towards the heart but the slit(s) will be closed by the blood flowing away from the heart. Alternately, the material may be punctured, for example by an introducer needle, which can then deliver the guidewire through the filter material and across the native valve. The valve delivery system is then advanced over the guidewire through the filter material and to the target site.

In FIG. 16B, the filter 124 is sized and shaped to be delivered in the aortic arch such that it contacts the walls of the arch. In FIG. 16C, the filter 124 is sized and shaped to be delivered across the opening of both the head and neck vessels at the same time. In this embodiment, the filter may exit the access sheath through a side port to aid in positioning the filter in the superior aspect of the aortic arch. In the embodiments shown in FIGS. 16B and 16C, the filter 124 is downstream of the sheath opening and the valve does not have to traverse the filter to be delivered. The embodiments in FIGS. 16B and 16C may be delivered through the main sheath lumen and be positioned in the aorta through the help of the pulsing blood flow leaving the heart. As the filters in FIGS. 16B and 16C are delivered out of the sheath and into the aorta, the blood flow tugs or pulls on the filter material and naturally aides to position the filter distal of the sheath. The devices resides in that position until removed back through the sheath at the end of the procedure.

Figure 17A:
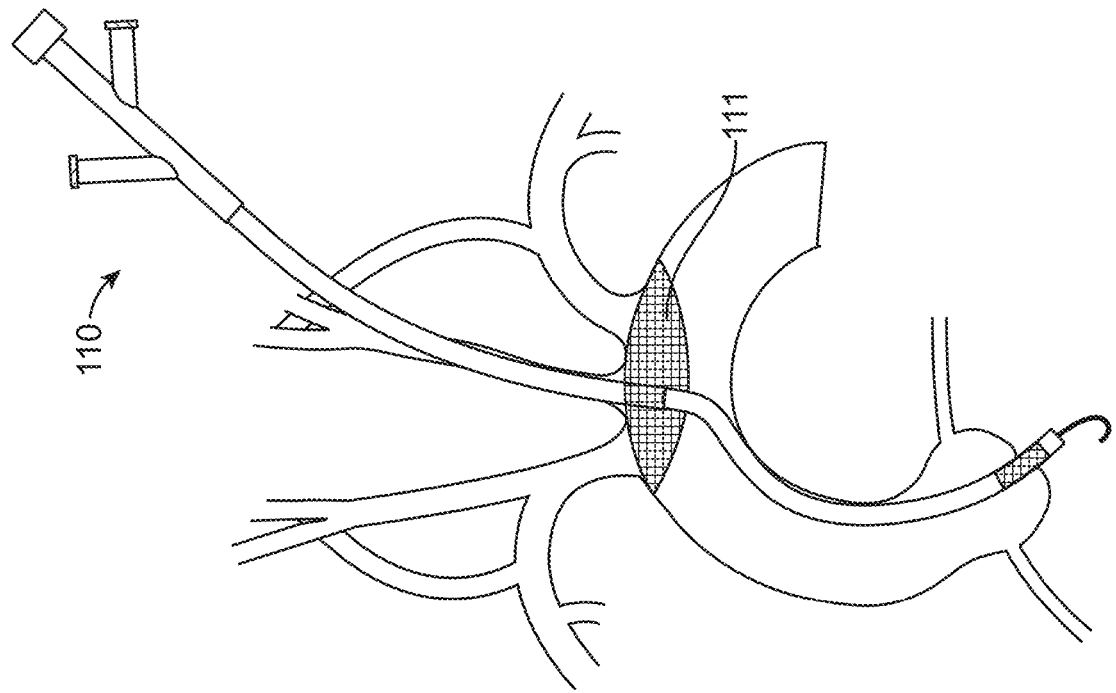
FIGS. 17A, 17B, 17C, and 17D show embodiments of an access sheath with a filter, wherein the filter is sized and shaped to be deployed in the aortic arch across the ostia of all the head and neck vessels or across the aortic arch.
Figure 17B:
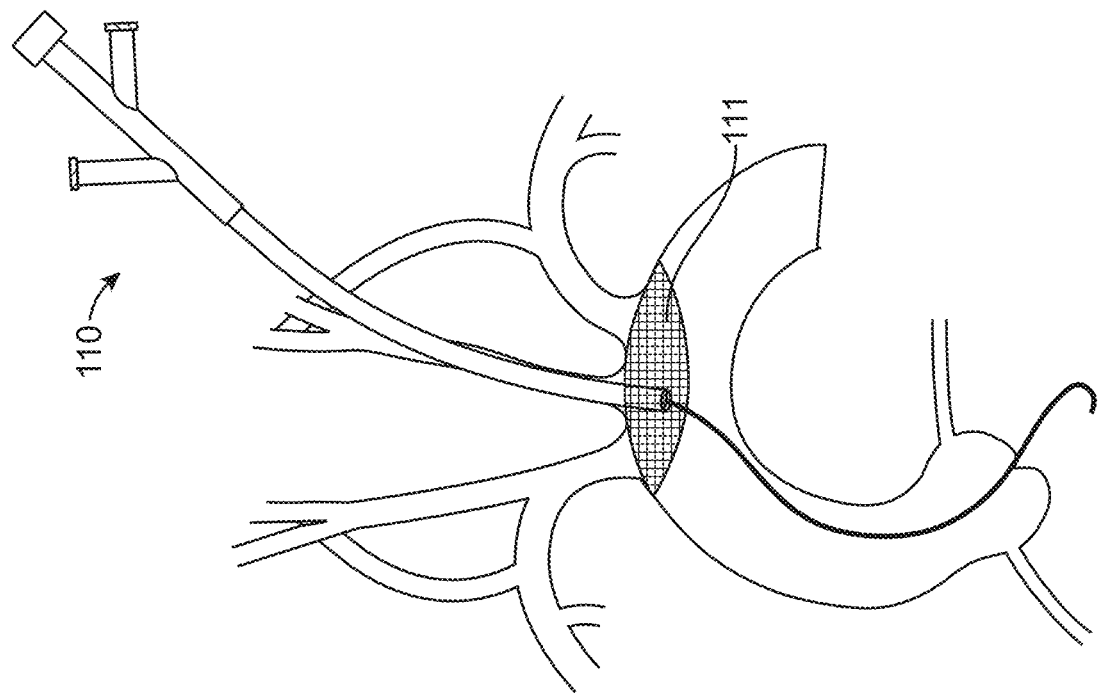
Figure 17C:
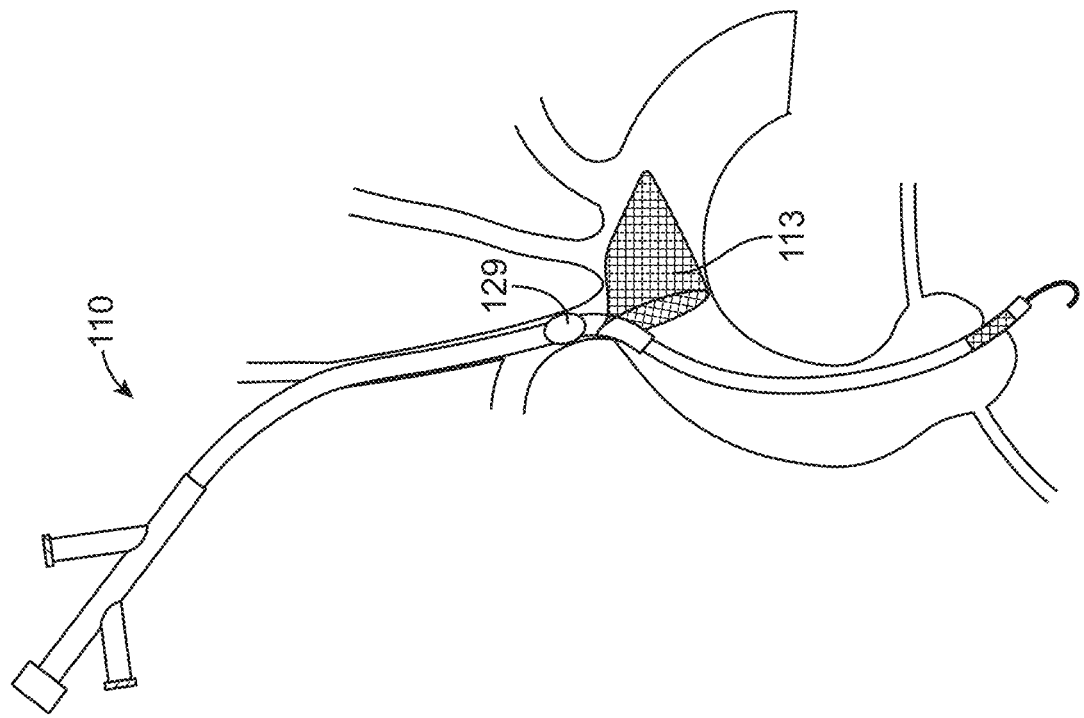
Figure 17D:
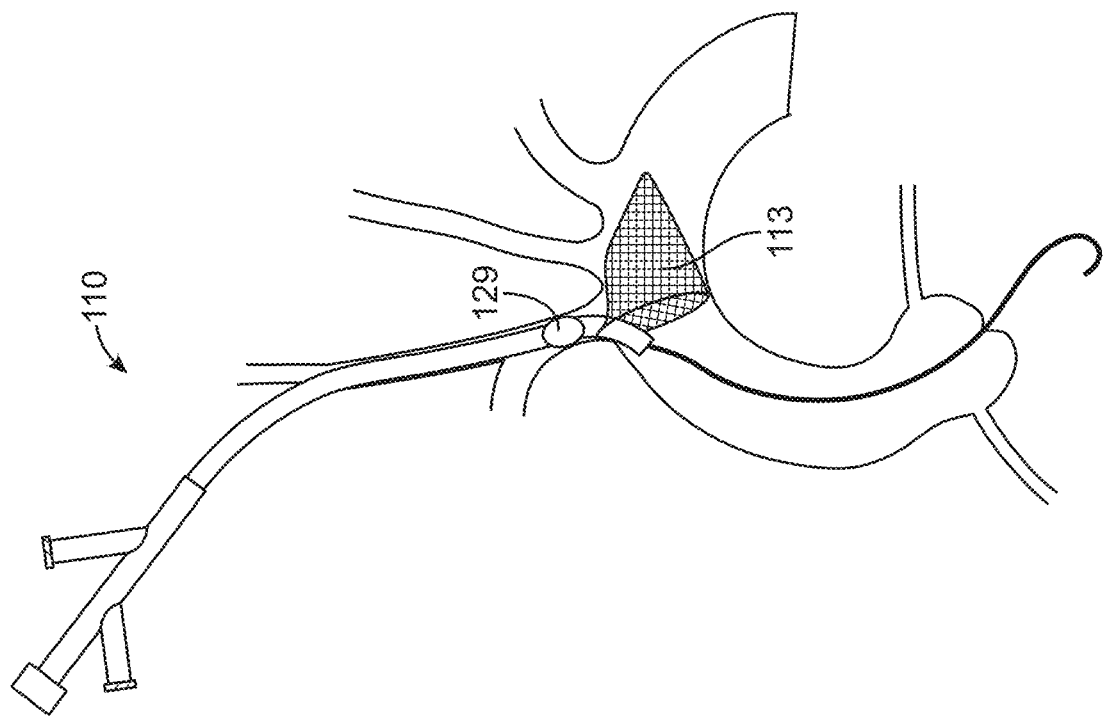

In another embodiment, shown in FIGS. 17A, 17B, 17C and 17D, an embolic filter is built onto or on the access sheath 110 and deployed in the aortic arch. In FIGS. 17A and 17B, the filter 111 is sized and shaped to be deployed across the superior aspect of the aortic arch, covering the ostia of some or all the head and neck vessels. In this embodiment, as both the access site carotid artery and the contralateral carotid artery are protected by the filter 111, an occlusion balloon is not required for embolic protection on the sheath during the valve implantation procedure. However, as there may be risk of embolic debris during deployment and retrieval of the filter, it may be desirable to retain the occlusion balloon and aspiration function as embolic protection during deployment of the filter prior to valve implantation, and retrieval of the filter after valve implantation. In FIGS. 17C and 17D, the aortic filter 113 is sized and shaped to be deployed across the aorta within the aortic arch, so that all downstream vessels are protected by the filter 113 from embolic debris during the valve implantation procedure.

Figure 18A:
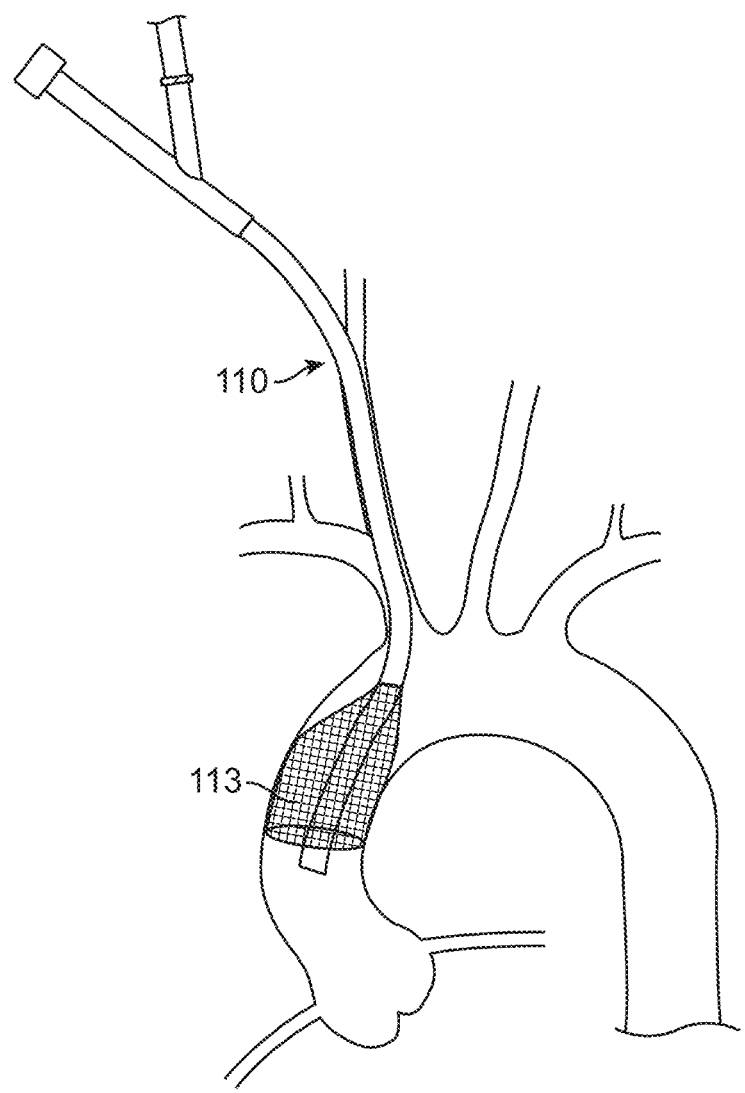
FIGS. 18A and 18B show alternate embodiments of an access sheath with a filter, wherein the filter is sized and shaped to be deployed in the ascending aorta
Figure 18B:
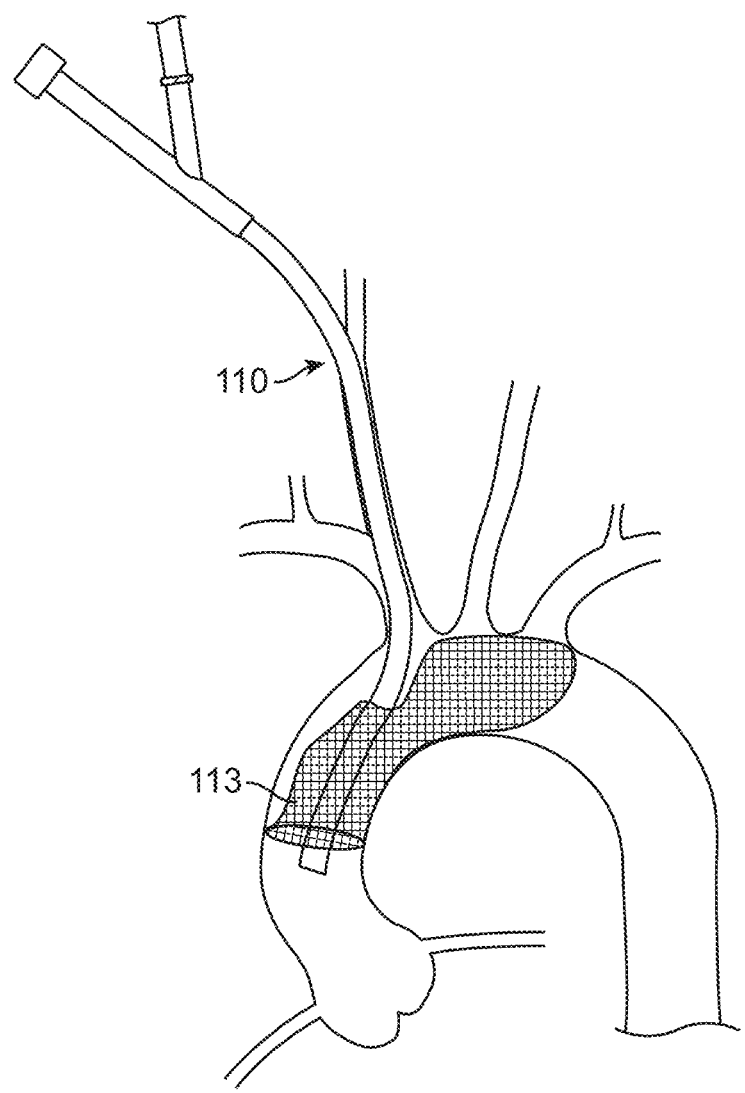

In another embodiment, shown in FIGS. 18A and 18B, the aortic filter is built onto or on the access sheath 110 and deployed in the ascending aorta. As shown in FIG. 18A, the aortic filter 113 is attached to the sheath 110 on the distal portion of the sheath. During use the distal portion of the access sheath is positioned in the ascending aorta, and then the filter 113 is expanded across the aorta so that all downstream vessels are protected by the filter. Deployment of the filter may be accomplished, for example, by a retractable sleeve on the outside of the sheath, which, when retracted, exposes the expandable filter. In one configuration, the filter deployed length may be varied depending on how much the retractable sleeve is pulled back. This control may allow the user to expand the filter to different sizes depending on the length and diameter the filter. Alternately, the filter may be pushed forward by a wire frame or structure to deploy the filter. As above, the amount of filter deployed may be varied depending on patient anatomy by varying how much of the frame to expose. In a variation of this embodiment, shown in FIG. 18A, the filter 113 instead could be occlusive to occlude the aorta during valve delivery rather than to filter the blood. In a variation of this embodiment, shown in FIG. 18B, the filter 113 is shaped to extend distally in the aorta. In this embodiment, the filter has a greater surface area and potentially has a lower effect on flow rate.

In any of the scenarios shown in FIGS. 15A-18B, an occlusion balloon 129 may be attached to the sheath 110 to block the accessed carotid artery. Additionally, during the step of filter retrieval after the valve is delivered, passive or active aspiration may be applied to the access sheath via Y-arm 112 to minimize the risk of embolic debris traveling to the downstream vessels. Optionally, irrigation may also be applied to assist in washing out loose debris, either through a channel in the sheath or via a separate irrigation catheter. As described above, the occlusion balloon 129 and aspiration and/or irrigation functions are not needed during the procedure as the aortic filter protects the access vessel; however, as described above, occlusion, aspiration and/or irrigation functions may be included in the system to provide protection during filter deployment and retrieval.

In all of the scenarios shown in FIGS. 15A-18B, the embolic filter material may be a perforated polymer film, a woven or knitted mesh material, or other material with a specific porosity. In an embodiment, the filter material porosity is between 80 and 150 microns. In an embodiment, the filter material porosity is between 100 and 120 microns. In an embodiment, the filter material is coated with heparin or other anti-coagulation agent, to prevent thrombus formation on the material during the procedure.

Figure 19:
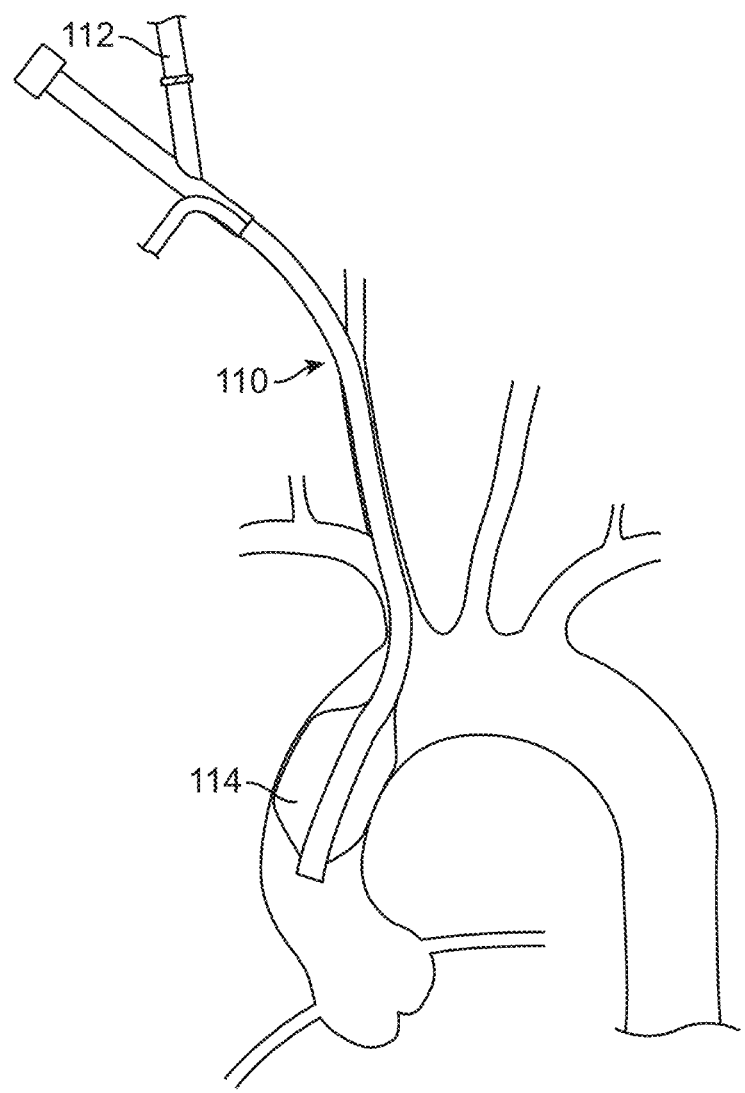
FIG. 19 shows an embodiment of an access sheath with an occlusion element, wherein the occlusion element is sized and shaped to be deployed in the ascending aorta

In another embodiment, as shown in FIG. 19, the access sheath 110 has an aortic occlusion element 114. The occlusion element is sized and shaped to occlude the ascending aorta. During use, the access sheath 110 is introduced via the right or left carotid artery and the distal portion is positioned in the ascending aorta. A pre-dilation balloon is positioned across the valve. Prior to pre-dilation of the valve, the heart flow is stopped or slowed significantly, e.g. via rapid pacing or atropine, and the occlusion element 114 is inflated or expanded to occlude the ascending aorta. The valve predilation step is then performed without risk of distal emboli. Prior to deflation of the occlusion element 114, aspiration may be applied to the ascending aorta via the side arm 112 of the sheath 110. Optionally, irrigation may also be applied to assist in washing out loose debris, either through a channel in the sheath or via a separate irrigation catheter.

After the occlusion element 114 is deflated, the heart flow may be resumed. Next, the valve is positioned for implantation. As with the previous step, the heart flow is stopped or slowed significantly, e.g. via rapid pacing or atropine, and the occlusion element 114 is inflated or expanded to occlude the expanding aorta. The valve implantation step is then performed without risk of distal emboli. Prior to deflation of the occlusion element 114, aspiration may be applied to the ascending aorta via the side arm 112 of the sheath 110. The occlusion element is then deflated and heart flow is resumed with the newly implanted valve in place. The balloon material could be formed to create a non-compliant, complaint or semi-compliant structure. The balloon may be formed from PET, Silicone, elastomers, Nylon, Polyethylene or any other polymer of co-polymer.

In this configuration, the occlusion element 114 may be a balloon, which is expanded by inflation with a fluid contrast media. In this configuration, the sheath includes an additional inflation lumen which can be connected to an inflation device. Alternately, the occlusion element may be a mechanically expandable occlusion element such as a braid, cage, or other expandable mechanical structure with a covering that creates a seal in the vessel when expanded.

Figure 20A:
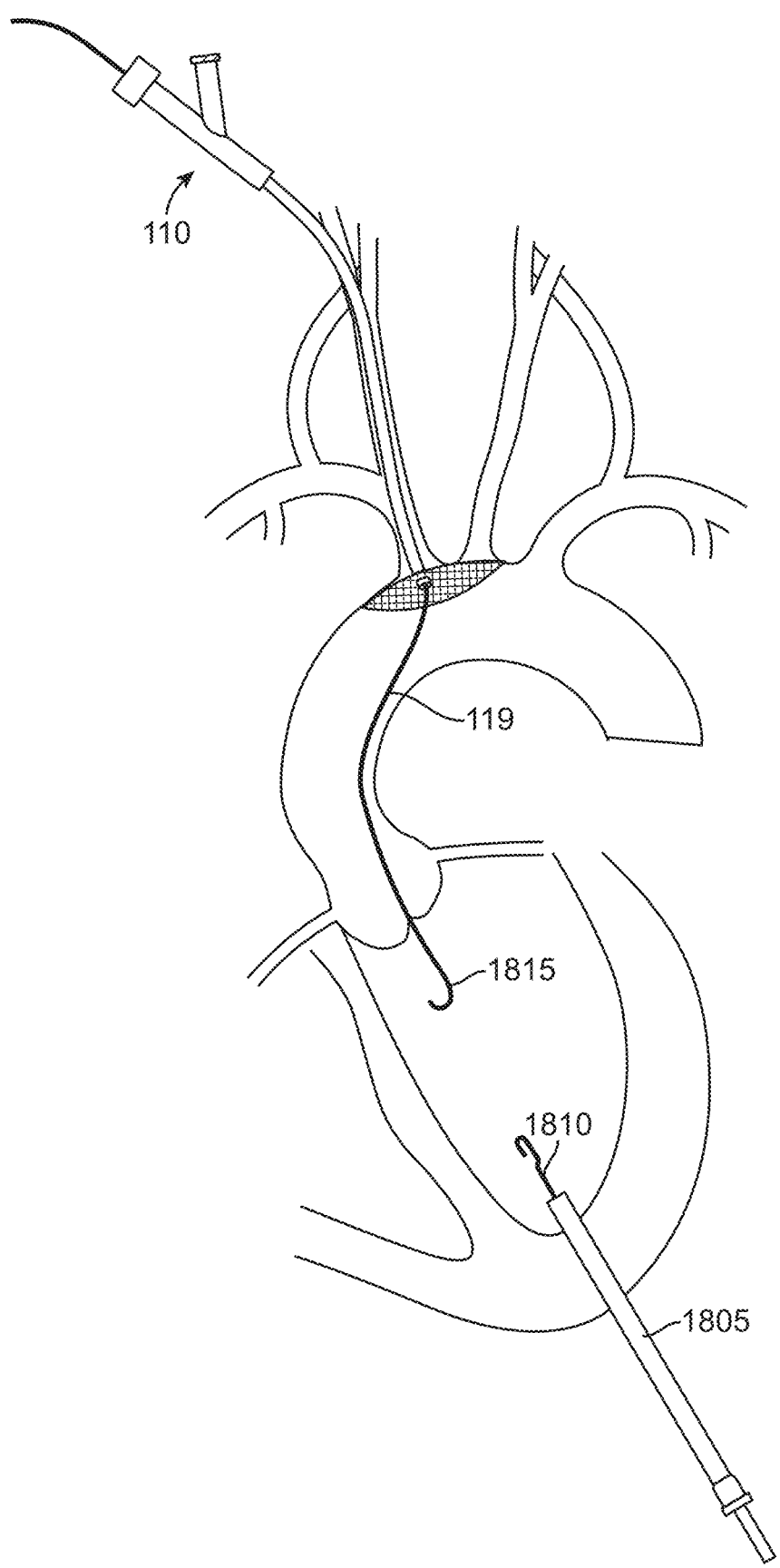
FIGS. 20A and 20B show alternate embodiments for delivering a prosthetic valve.
Figure 20B:
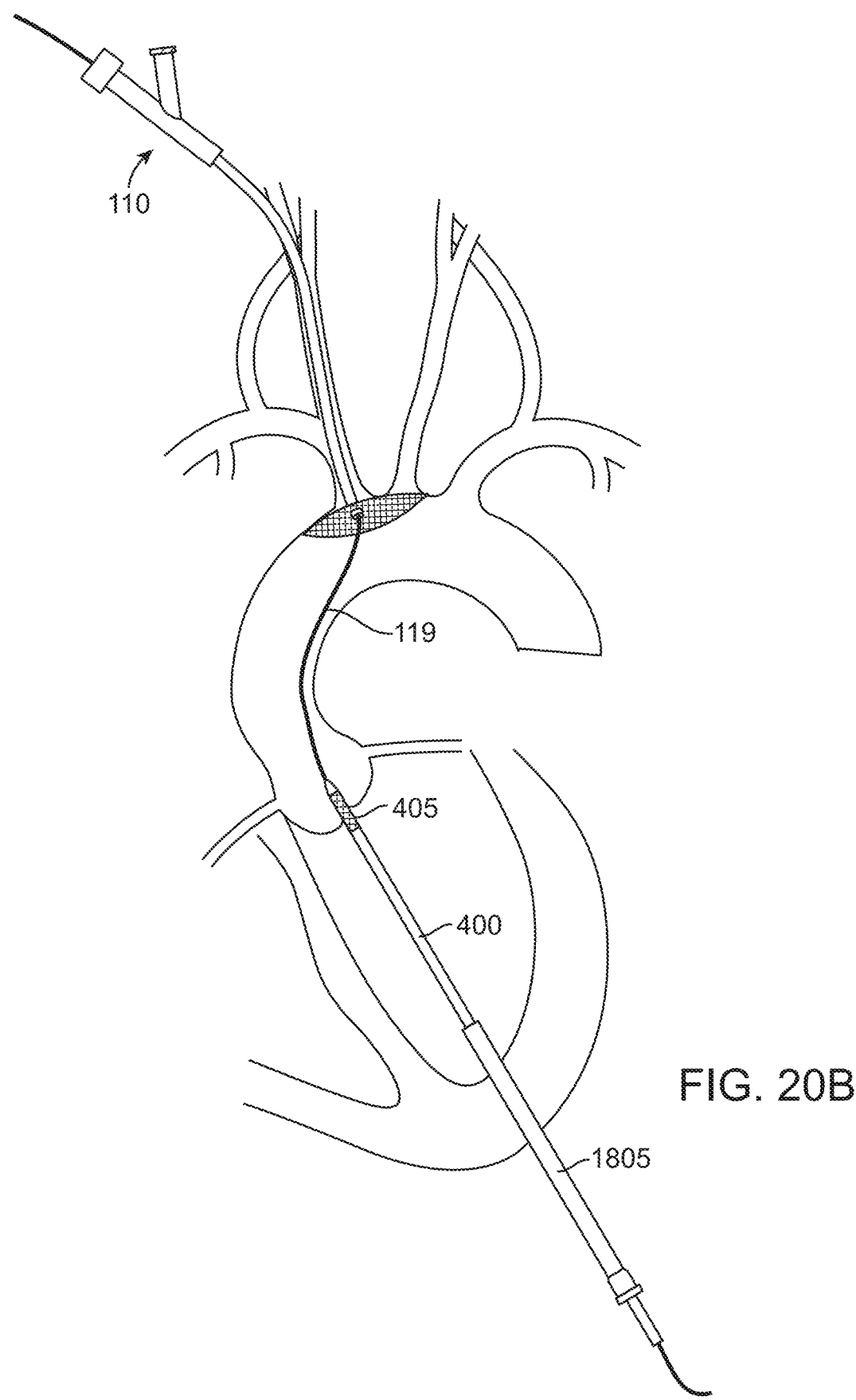

In another configuration, shown in FIGS. 20A and 20B, a first access sheath 110 is deployed transcarotidly into the artery so as to provide access to the aortic valve. The first access sheath 110 is configured as described above so that it can be used to provide cerebral embolic protection and to introduce a guide wire 119 into the vasculature and across the aortic valve. In addition, a second access sheath 1805 is introduced via alternate access site to access the aortic annulus from the other side, for example a transapical access site into the left ventricle. The second access sheath 1805 can be used to introduce a delivery system 400 which has been configured for transapical access for implanting the prosthetic valve 405. In this embodiment, the second access sheath 1805 may first be used to introduce a snare device 1810 that is configured to grasp or otherwise snare the distal end 1815 of the guide wire 119 that was inserted through the first access sheath 110, as in FIG. 20A. Alternately, as in FIG. 20B, the snare 1810 may be introduced via the first access sheath 110 and the guidewire 119 introduced via the second access sheath 1805. Irrespective of which end the guidewire was introduced or snared, the snare may be pulled back so that both ends of the guidewire may be secured externally. Such a double-ended securement of the guidewire 119 provides a more central, axially oriented and stable rail for placement of the prosthetic valve 405 than in a procedure where the guidewire distal end is not secured. The prosthetic valve 405 can then be positioned over the guidewire 119 via the second access sheath 1805, and deployed in the aortic annulus. In this embodiment, the first sheath 110 may be smaller than the second access sheath 1805, as the first sheath 110 does not require passage of a transcatheter valve.

In a variation of the embodiment of FIGS. 20A and 20B, a transcarotid valve delivery system 200 and valve 205 may be delivered via the first sheath 110, as shown in FIG. 21. An advantage of this approach is that it requires a smaller puncture in the apex of the heart than the approach of FIGS. 20A and 20B. However a larger sheath is required in the first, access site. In this method embodiment, the first access site is shown as a transcarotid access in FIGS. 20 and 21, but may also be a sub-clavian or transfemoral access site.

Figure 24:
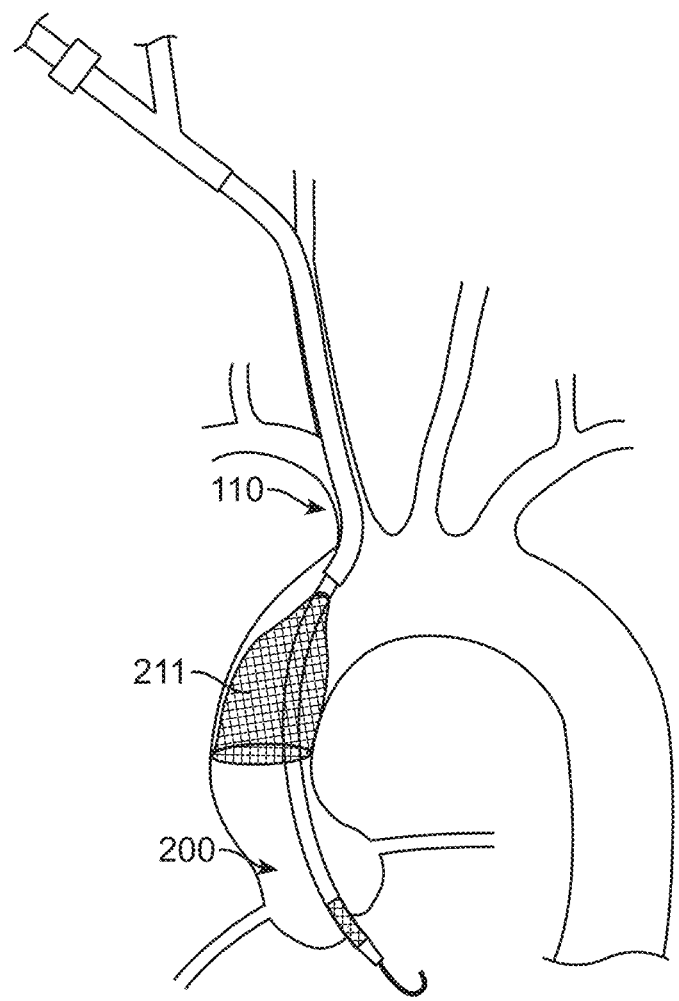
FIG. 24 shows an embodiment of a transcarotid prosthetic aortic valve and delivery system with a filter element.

In another embodiment, the transcarotid valve delivery system also includes distal embolic protection elements. A shown in FIG. 24, the valve delivery system 200 includes an expandable filter element 211 that is sized and shaped to be expanded across the ascending when the valve delivery system 200 is positioned to deploy the valve in the desired location. Deployment of the filter may be accomplished by a retractable sleeve on the outside of the sheath, which, when retracted, exposes the expandable filter. Alternately, the filter may be pushed forward by means of a wire frame or structure to deploy the filter. The filter element may be affixed to the pusher sleeve 230 of the valve delivery system, or it may be affixed to a movable outer sleeve so that it can be independently positioned with respect to the valve. In the latter variation, the filter may be positioned and expanded before the valve has crossed the native valve location, thus protecting downstream flow from distal emboli during the crossing step of the procedure.

Figure 25:
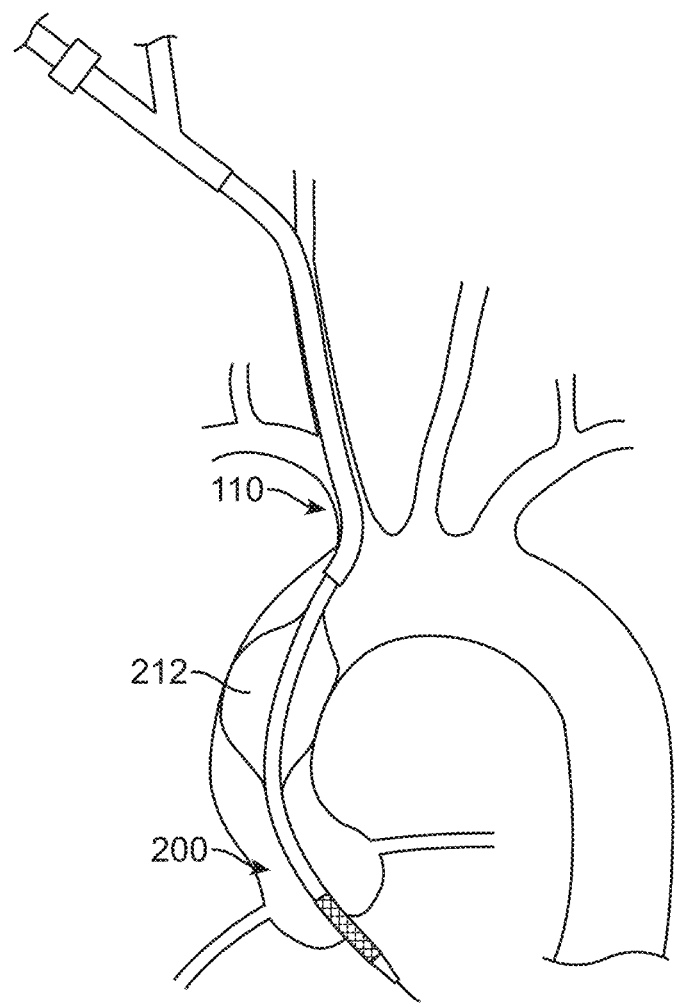
FIG. 25 shows an embodiment of a transcarotid prosthetic aortic valve and delivery system with an occlusion element.

In a variation of this embodiment, as shown in FIG. 25, the valve delivery system 200 includes an occlusion element 212 which is sized and shaped to occlude the ascending when the valve delivery system 200 is positioned to deploy the valve in the desired location. The occlusion element 212 may be a balloon, which is expanded by inflation with a fluid contrast media. In this configuration, the valve delivery system 200 includes an additional inflation lumen which can be connected to an inflation device. Alternately, the occlusion element may be a mechanically expandable occlusion element such as a braid, cage, or other expandable mechanical structure with a covering that creates a seal in the vessel when expanded. The occlusion element may be affixed to the pusher sleeve 230 of the valve delivery system, or it may be affixed to a movable outer sleeve so that it can be independently positioned with respect to the valve.

If the access to the carotid artery was via a surgical cut down, the access site may be closed using standard vascular surgical techniques. Purse string sutures may be applied prior to sheath insertion, and then used to tie off the access site after sheath removal. If the access site was a percutaneous access, a wide variety of vessel closure elements may be utilized. In an embodiment, the vessel closure element is a mechanical element which include an anchor portion and a closing portion such as a self-closing portion. The anchor portion may comprise hooks, pins, staples, clips, tine, suture, or the like, which are engaged in the exterior surface of the common carotid artery about the penetration to immobilize the self-closing element when the penetration is fully open. The self-closing element may also include a spring-like or other self-closing portion which, upon removal of the sheath, will close the anchor portion in order to draw the tissue in the arterial wall together to provide closure. Usually, the closure will be sufficient so that no further measures need be taken to close or seal the penetration. Optionally, however, it may be desirable to provide for supplemental sealing of the self-closing element after the sheath is withdrawn. For example, the self-closing element and/or the tissue tract in the region of the element can be treated with hemostatic materials, such as bioabsorbable polymers, collagen plugs, glues, sealants, clotting factors, or other clot-promoting agents. Alternatively, the tissue or self-closing element could be sealed using other sealing protocols, such as electrocautery, suturing, clipping, stapling, or the like. In another method, the self-closing element will be a self-sealing membrane or gasket material which is attached to the outer wall of the vessel with clips, glue, bands, or other means. The self-sealing membrane may have an inner opening such as a slit or cross cut, which would be normally closed against blood pressure. Any of these self-closing elements could be designed to be placed in an open surgical procedure, or deployed percutaneously.

In an alternate embodiment, the vessel closure element is a suture-based vessel closure device. The suture-based vessel closure device can place one or more sutures across a vessel access site such that, when the suture ends are tied off after sheath removal, the stitch or stitches provide hemostasis to the access site. The sutures can be applied either prior to insertion of a procedural sheath through the arteriotomy or after removal of the sheath from the arteriotomy. The device can maintain temporary hemostasis of the arteriotomy after placement of sutures but before and during placement of a procedural sheath and can also maintain temporary hemostasis after withdrawal of the procedural sheath but before tying off the suture. U.S. patent application Ser. No. 12/834,869 entitled "SYSTEMS AND METHODS FOR TREATING A CAROTID ARTERY", which is incorporated herein by reference in its entirety, describes exemplary closure devices and also describes various other devices, systems, and methods that are related to and that may be combined with the devices, systems, and methods disclosed herein.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A system for transcatheter aortic valve treatment, comprising:
    an arterial access sheath adapted to be introduced into an access site at the left or right carotid artery, or left or right subclavian artery,
        wherein the arterial access sheath has a first lumen configured to receive a valve delivery system, the valve delivery system configured to deliver a prosthetic valve into a heart or aorta through the arterial access sheath, the first lumen having a first opening at a proximal end of the arterial access sheath and a distal opening at a distal most end of the arterial access sheath;
        wherein the arterial access sheath further has a perfusion lumen with a proximal end and a distal opening and wherein the perfusion lumen has a length such that the distal opening of the perfusion lumen can be positioned in and perfuse an artery when in use;
    an elongated body having a shunt lumen, the elongated body configured to fluidly connect an external source of perfusion fluid to the perfusion lumen of the arterial access sheath, wherein the elongated body receives perfusion fluid only from a source of perfusion fluid other than the arterial access sheath; and
    the valve delivery system, wherein the valve delivery system fits within the first lumen of the arterial access sheath.

2. A system as in claim 1, wherein the distal opening of the perfusion lumen has a radiopaque marker.

3. A system as in claim 1, wherein the arterial blood source comprises a sheath in a femoral artery.

4. A system as in claim 1, wherein the shunt incorporates an active pump.

5. A system as in claim 1, wherein the shunt further comprises an in-line filter.

6. A system as in claim 1, wherein the access sheath further comprises an occlusion balloon at a distal end of the access sheath.

7. A system as in claim 1, wherein the shunt does not include a filter.

8. A system as in claim 1, wherein the artery that is perfused is the carotid artery.

9. A system as in claim 1, wherein the proximal end of the first lumen has a proximal connector with a hemostasis valve and a Y-arm, and wherein the hemostasis valve is sized to fit therethrough the valve delivery system.

10. A system as in claim 1, wherein the valve delivery system includes:
    an inner shaft;
    an outer sleeve co-axially aligned with the inner shaft and slidably positioned over the inner shaft;
    a prosthetic aortic valve removably mounted on the inner shaft; and
    an actuator coupled to the outer shaft, wherein the actuator can be actuated to retract the outer shaft from a first position to a second position that exposes the prosthetic aortic valve.

11. A system as in claim 10, wherein the valve delivery system has an entire length between 45 cm and 60 cm.

* * * * *